United States Patent

Nakao et al.

[11] Patent Number: 5,997,547
[45] Date of Patent: *Dec. 7, 1999

[54] SURGICAL RETRIEVAL ASSEMBLY AND ASSOCIATED METHOD

[76] Inventors: Naomi L. Nakao, 303 E. 57th. St., New York, N.Y. 10022; Peter J. Wilk, 185 W. End Ave., New York, N.Y. 10023

[*] Notice: This patent is subject to a terminal disclaimer.

[21] Appl. No.: 09/062,185

[22] Filed: Apr. 17, 1998

Related U.S. Application Data

[63] Continuation of application No. 08/700,562, Aug. 8, 1996, Pat. No. 5,741,271, which is a continuation-in-part of application No. 08/333,363, Nov. 2, 1994, Pat. No. 5,759,187, which is a continuation-in-part of application No. 08/213,196, Mar. 14, 1994, Pat. No. 5,486,182, which is a continuation-in-part of application No. 08/012,657, Feb. 1, 1993, Pat. No. 5,336,227, which is a continuation-in-part of application No. 07/788,035, Nov. 5, 1991, Pat. No. 5,201,740, and application No. 07/892,214, Jun. 2, 1992, Pat. No. 5,190,542, said application No. 08/333,363, is a continuation-in-part of application No. 07/957,416, Oct. 5, 1992, Pat. No. 5,374,273.

[51] Int. Cl.[6] .............................. A61B 17/24; A61B 17/26
[52] U.S. Cl. ........................... 606/114; 606/110; 606/113
[58] Field of Search .................................. 606/110, 114, 606/113, 127, 185; 600/564, 562

[56] References Cited

U.S. PATENT DOCUMENTS

| | | | |
|---|---|---|---|
| 4,598,699 | 7/1986 | Garren et al. | 606/185 |
| 5,234,439 | 8/1993 | Wilk et al. | 606/113 |
| 5,290,284 | 3/1994 | Adair | 606/46 |
| 5,336,227 | 8/1994 | Nakao et al. | 606/110 |
| 5,342,297 | 8/1994 | Jang | 604/280 |
| 5,352,184 | 10/1994 | Goldberg et al. | 606/127 |
| 5,423,830 | 6/1995 | Schneebaum et al. | 606/110 |
| 5,451,206 | 9/1995 | Young | 604/280 |
| 5,465,731 | 11/1995 | Bell et al. | 600/564 |
| 5,542,948 | 8/1996 | Weaver et al. | 606/110 |
| 5,571,093 | 11/1996 | Cruz et al. | 604/280 |
| 5,611,803 | 3/1997 | Heaven et al. | 606/114 |

Primary Examiner—Richard J. Apley
Assistant Examiner—Justine R. Yu
Attorney, Agent, or Firm—R. Neil Sudol; Henry D. Coleman

[57] ABSTRACT

A surgical instrument assembly for a snare cauterization operation comprises a tubular member having a diameter sufficiently small so that the tubular member can be inserted through a biopsy channel of a flexible endoscope. Multiple endoscopic instrument including a cauterization loop, a flexible web member connected to the cauterization loop or to an auxiliary loop so as to form a capture pocket, and an elongate flexible fluid feed tube provided at a distal end with a needle point and an aperture, are slidably disposed in the tubular member. The fluid feed instrument is used to expand a flat or nonprojecting polyp prior to severing thereof with the cauterization loop and capture of the severed polyp with the web member or pocket.

18 Claims, 15 Drawing Sheets

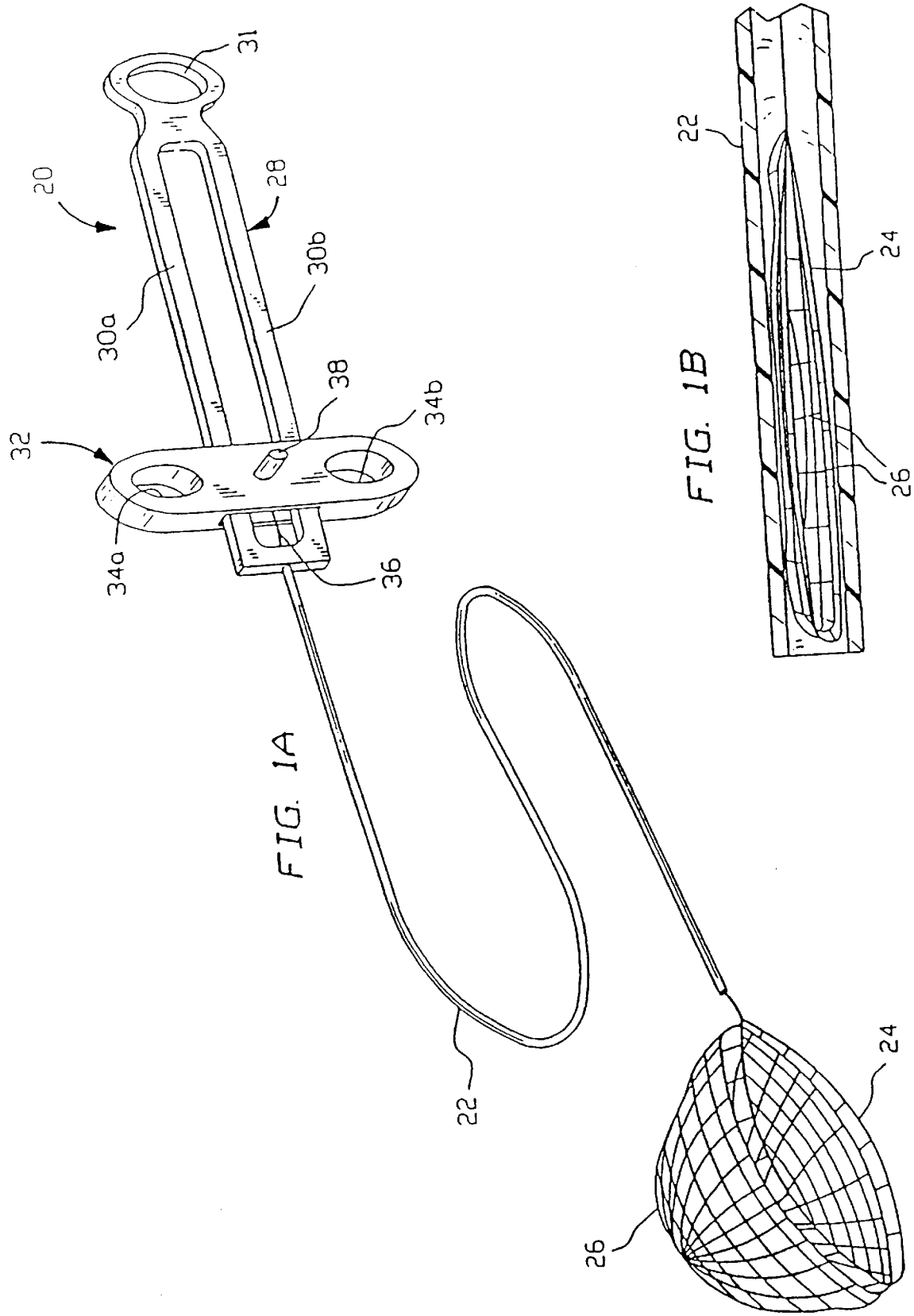

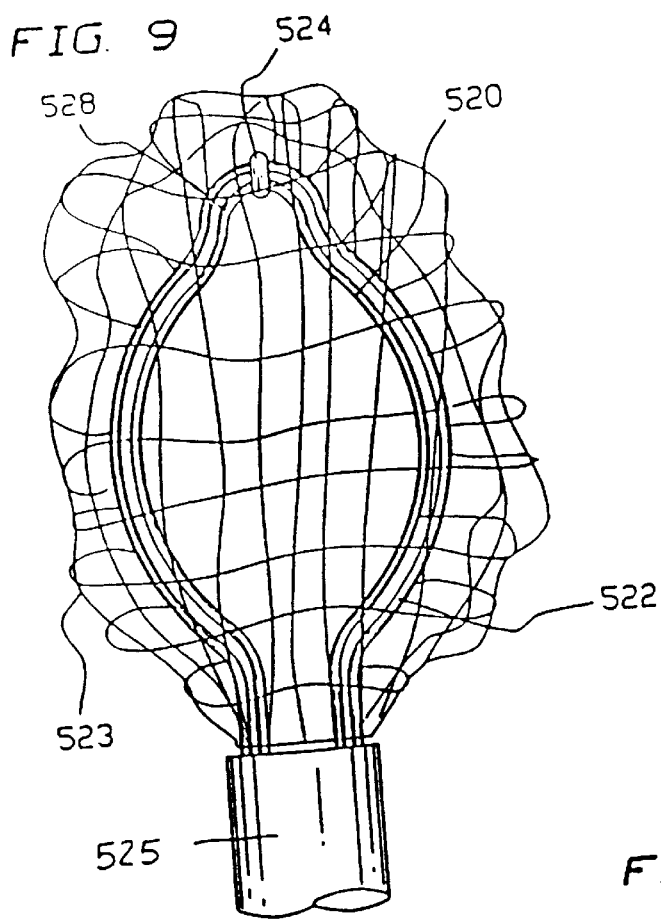
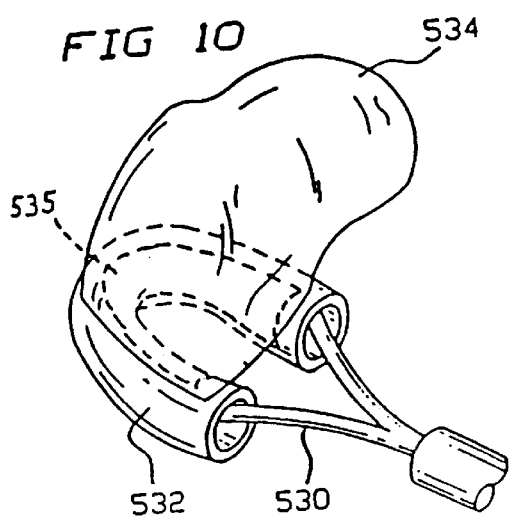
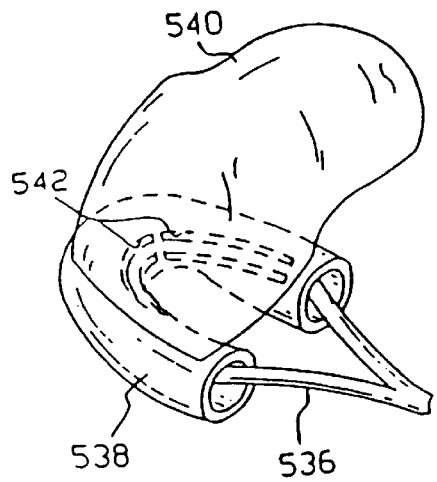

SURGICAL RETRIEVAL ASSEMBLY AND ASSOCIATED METHOD

CROSS-REFERENCE TO RELATED APPLICATIONS

This application is a continuation of application Ser. No. 08/700,562 filed Aug. 8, 1996, now U.S. Pat. No. 5,741,271, continuation-in-part of commonly owned application Ser. No. 08/333,363, filed Nov. 2, 1994, now U.S. Pat. No. 5,759,187, which is a continuation-in-part of application Ser. No. 08/213,196, filed Mar. 14, 1994, now U.S. Pat. No. 5,486,182. application Ser. No. 08/213,196 was filed as a continuation-in-part of commonly owned application Ser. No. 08/012,657, filed Feb. 1, 1993, now U.S. Pat. No. 5,336,227. Application Ser. No. 08/012,657 was filed as a continuation-in-part of commonly owned application Ser. No. 07/788,035 filed Nov. 5, 1991, now U.S. Pat. No. 5,201,740, and a continuation-in-part of commonly owned application Ser. No. 07/892,214 filed Jun. 2, 1992, now U.S. Pat. No. 5,190,542. Application Ser. No. 08/333,363 is also a continuation-in-part of commonly owned application Ser. No. 07/957,416 filed Oct. 5, 1992, now U.S. Pat. No. 5,374,273.

FIELD OF THE INVENTION

This invention relates to a surgical instrument assembly for use in removing and retrieving selected tissues from internal body cavities of a patient. This invention more specifically relates to an instrument assembly for use in snare cauterization operations. This invention also relates to an associated method for severing internal organic tissues and retrieving the severed organic tissues from the patient. More specifically, the present invention relates to a method for removing polyps.

BACKGROUND OF THE INVENTION

In a conventional endoscopic snare operation, an endoscope is inserted into an internal cavity of a patient, e.g., into the colon, and is used to locate abnormal tissue growths such as polyps in the internal cavity. Upon the locating of a polyp or other growth which is to be removed, a wire extending through a tube in the biopsy channel of the endoscope is slid in the distal direction so that a cauterization loop connected to the wire is ejected from the distal end of the tube and the endoscope. The loop and the endoscope are manipulated from outside of the patient to pass the loop over the polyp or growth. The wire is then withdrawn in the proximal direction to tighten the loop around a base region or neck of the polyp. Once the loop is in contact with the base region of the polyp, an electrical current is conducted through the loop via the wire. Generally, as the loop is closed about the base region of the polyp, electrical current is transmitted through the narrowed organic tissues and thereby generates therein heat sufficiently great to cut and cauterize.

Once a polyp is severed by such a snare cauterization technique, it frequently becomes difficult to capture the polyp and retrieve it from the patient. Sometimes the cauterization loop is used in an effort to ensnare the polyp. Other capture techniques involve the use of forceps or the application of suction. In using forceps, the snare cauterization tube is removed from the biopsy channel of the endoscope and replaced with the forceps. In using suction, a vacuum is applied via a suction channel of the endoscope.

No matter which specific technique is used, the polyp frequently escapes from the capturing instrumentality and falls away into the colon (or other cavity). Especially in cases where the polyp is large, the effort and time expended in retrieving the severed polyp may rival or even exceed the effort and time required to locate and sever the polyp. In some cases, the endoscope must be removed without the polyp and the patient given an enema in an attempt to flush out the polyp from the colon.

Furthermore, there are numerous cases where a severed polyp is never recovered. Sometimes, the polyp is macerated during the retrieval attempt. In all such cases, the pathologist is unable to determine whether the polyp contains carcinoma in situ (localized) or infiltrative carcinoma (spread). The patient must then undergo a colon resection sometimes unnecessarily.

In any event, the manipulations necessary to remove a severed polyp generally increase the trauma to the patient, the expense of the surgery and the hospitalization time. There is now a long-felt need to improve the snare cauterization technique to facilitate the capture and retrieval of severed polyps.

U.S. Pat. No. 5,201,740 to Nakao et al. provides a solution to the above-described problems in polyp removal. Pursuant to the disclosure of that patent, snare cauterization operations are performed with a surgical instrument assembly comprising a tubular sheath member carrying a metallic cauterization loop and a metal wire operatively connected to the loop, the wire passing longitudinally through the sheath. An electrical supply is operatively connectable to the wire, while a flexible web member is connected to the loop to form a capture pocket, the loop defining a mouth opening of the pocket. During use of the snare cauterization loop, the web member is passed over and substantially surrounds a polyp. The pocket captures the polyp at the same time that the cauterization loop is energized to effectuate a severing of the polyp.

This cauterization snare assembly with attached pocket is a substantial advance over conventional polyp removal techniques. However, in some cases, the pocket can obscure the polyp from visualization via the endoscope's optical system, making it difficult to obtain an optimal severing of the polyp. For example, if a polyp is located behind a fold of colonic tissues, it can be difficult to manipulate a cauterization snare to place it around the polyp. If a pouch is attached to the cauterization loop, the pouch may inhibit effective visualization of the polyp, thereby increasing the difficulty of the cauterization snare procedure.

Another problem in the removal of polyps occurs where a polyp lies flat against the wall of the colon or other internal body cavity. In this case it is difficult for the snare to encircle and sever the polyp. Some progress has been made in this regard by injecting saline or other fluid into the polyp, or into a base region thereof. This injection serves to expand the tissues and elevate the polyp from the internal organic wall, thereby facilitating snare use. The polyp injection operation is currently performed by a separate instrument which must be removed prior to the insertion of a cauterization snare.

OBJECTS OF THE INVENTION

An object of the present invention is to provide an improved method for the removal of polyps and other organic tissue parts from patients, particularly a method useful for removing polyps which lie flattened against the wall of the colon or other internal organ.

A more specific object of the present invention is to provide an improved method for the performance of a snare cauterization operation, particularly a method useful for removing polyps which lie flattened against the wall of the colon or other internal organ.

A further object of the present invention is to provide an instrument assembly for use in removing polyps and other tissue clumps from patients, particularly for removing polyps which lie flattened against the wall of the colon or other internal organ.

Another particular object of the present invention is to provide such an instrument assembly which is simple to manufacture and therefore inexpensive.

A further particular object of the present invention is to provide such an instrument assembly which is easy to use.

These and other objects will be apparent from the following descriptions.

BRIEF DESCRIPTION

A surgical instrument assembly for use in snare cauterization operations comprises, in accordance with an embodiment of the present invention, a tubular member having a diameter sufficiently small so that the tubular member can be inserted through a biopsy channel of a flexible endoscope, a cauterization loop, an electrically conductive wire operatively connected to the cauterization loop, the cauterization loop and the wire being disposed at least partially in the tubular member, an electrical connector operatively connected to the wire for feeding an electrical current to the cauterization loop via the wire, an auxiliary loop, an elongate flexible shifting member connected at one end to the auxiliary loop, the auxiliary loop and the shifting member being at least partially disposed in the tubular member, a flexible web member connected to the auxiliary loop so as to form a capture pocket, the auxiliary loop defining a mouth opening of the pocket, an elongate flexible tube provided at a distal end with a needle point and an aperture, the flexible tube being disposed at least partially in the tubular member, and a fluid feed operatively connected to the flexible tube for feeding fluid thereto for ejection through the aperture.

It is contemplated that the tubular member may be provided with a septum or a plurality of septums defining at least three separate longitudinally extending lumens, the flexible tubes extending through respective lumens.

In use of this instrument assembly during an endoscopic tissue removal operation, the tubular member is disposed in a biopsy channel of an endoscope which is inserted into a patient. The endoscope is used to visually monitor internal body tissues of the patient. Upon a detection of selected internal tissues to be removed from the patient, the flexible tube is shifted in the distal direction to eject the needle point from the tubular member, whereupon the needle point and the aperture are inserted into the selected internal tissues, which are disposed along an internal organic wall of the patient. Liquid is then forced through the flexible tube and the aperture into the selected internal tissues of the patient to expand the tissues and thereby induce the tissues to stand away from the internal organic wall. During the operation, the cauterization loop is shifted in a distal direction relative to the tubular member to eject the cauterization loop from the tubular member. The ejected cauterization loop is at least partially expanded from a collapsed configuration and passed over the expanded internal tissues of the patient, whereupon the cauterization loop is closed. An electrical current is conducted along the wire to the closed cauterization loop to sever the expanded internal tissues. In addition, the operation includes the ejection of the auxiliary loop from the tubular member, the opening of the auxiliary loop from a folded configuration, and the passing of the opened auxiliary loop over the expanded internal tissues so that the web member substantially surrounds the expanded internal tissues. After the severing of the expanded internal tissues by the cauterization loop and after passing of the auxiliary loop over the expanded internal tissues, the auxiliary loop is at least partially closed to capture the severed internal body tissues in the pocket.

A surgical instrument assembly for use in snare cauterization operations comprises, in accordance with another embodiment of the invention, a tubular member having a diameter sufficiently small so that the tubular member can be inserted through a biopsy channel of a flexible endoscope, a cauterization loop, an electrically conductive wire operatively connected to the cauterization loop, an electrical connector operatively connected to the wire for feeding an electrical current to the cauterization loop via the wire, a flexible web member connected to the cauterization loop so as to form a capture pocket, an elongate flexible tube provided at a distal end with a needle point and an aperture, and a fluid feed operatively connected to the flexible tube for feeding fluid thereto for ejection through the aperture. The cauterization loop and the wire, as well as the flexible tube, are disposed at least partially in the tubular member. The cauterization loop defines a mouth opening of the pocket.

In using this second embodiment during an endoscopic tissue removal operation, the tubular member is disposed in a biopsy channel of an endoscope which is inserted into a patient. The endoscope is used to visually monitor internal body tissues of the patient. Upon a detection of selected internal tissues to be removed from the patient, the flexible tube is shifted in the distal direction to eject the needle point from the tubular member, whereupon the needle point and the aperture are inserted into the selected internal tissues, which are disposed along an internal organic wall of the patient. Liquid is then forced through the flexible tube and the aperture into the selected internal tissues of the patient to expand the tissues and thereby induce the tissues to stand away from the internal organic wall. During the operation, the cauterization loop is shifted in a distal direction relative to the tubular member to eject the cauterization loop and the web member from the tubular member. The ejected cauterization loop is at least partially expanded from a collapsed configuration and passed, together with the web member, over the expanded internal tissues of the patient, whereupon the cauterization loop is closed. An electrical current is conducted along the wire to the closed cauterization loop to sever the expanded internal tissues. After the severing of the expanded internal tissues by the cauterization loop, the severed internal body tissues are disposed in the pocket.

The present invention provides an improved method and an associated instrument assembly for the removal of flat or receding polyps from patients via snare cauterization. A fluid injection needle is introducible into a hollow internal organ together with a snare cauterization and capture pocket assembly, thereby eliminating the necessity of instrument removal prior to the insertion of another instrument required for the completion of the operation.

In a method in accordance with the present invention, the severing, capture and retrieval of flat or nonprojecting polyps are facilitated. An instrument assembly in accordance with the present invention is simple to use. Accordingly, trauma to the patient and time in surgery are reduced. More specifically, time under anaesthesia with the accompanying side effects is reduced. Concomitantly, the expense of hospitalization is decreased.

An instrument assembly in accordance with the present invention allows one to sever a flat or nonprojecting polyp and then to subsequently capture the severed polyp before it has a chance to roll away. The capture pocket may be placed about the polyp after the cauterization loop is in place and before cutting occurs. Alternatively, the capture pocket or pouch may be ejected from the common tubular instrument guide only after the cauterization operation is completed. In either case, the capture pocket remains out of the way until the cauterization loop is placed over the polyp and is in place for the cauterization operation.

BRIEF DESCRIPTION OF THE DRAWING

FIG. 1A is a schematic perspective view of a snare cauterization instrument assembly, showing a cauterization loop in an ejected, use configuration.

FIG. 1B is a schematic longitudinal cross-sectional view of a distal end of the cauterization instrument assembly of FIG. 1A, showing the cauterization loop in a withdrawn or retracted storage configuration inside the distal end of a tubular member of the instrument assembly.

FIG. 9 is a schematic top view of another modified snare cauterization instrument assembly, showing an auxiliary loop attached at one point to a cauterization loop.

FIG. 10 is a schematic partial perspective view, on an enlarged scale, of an additional snare cauterization instrument assembly.

FIG. 11 is a schematic partial perspective view, on an enlarged scale, of yet a further snare cauterization instrument assembly.

The same elements and organs in the different figures bear the same reference designations.

DESCRIPTION OF THE PREFERRED EMBODIMENTS

Figure 2A:
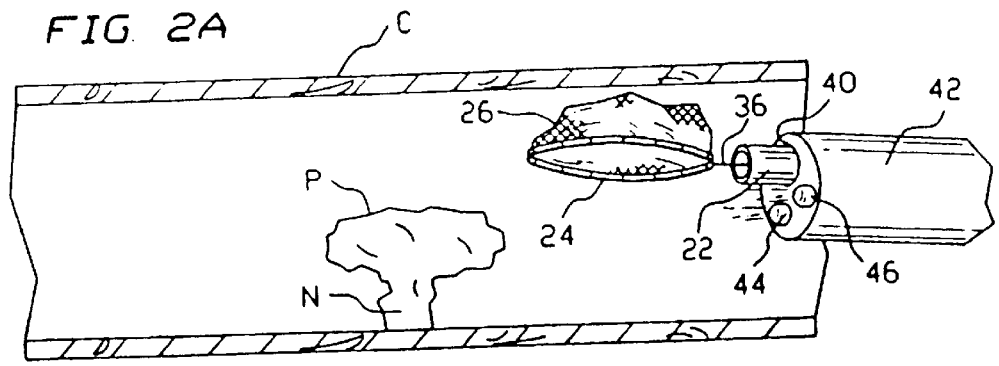
FIG. 2A is a schematic partial cross sectional view of a patient's colon with a polyp, showing the snare cauterization instrument assembly of FIG. 1A inserted in the biopsy channel of an endoscope which is itself inserted into the patient's colon, and further showing the instrument assembly in an initial stage of a snare cauterization procedure.

As illustrated in FIG. 1A, a snare cauterization instrument assembly comprises a hand held control module 20, a flexible tubular member 22 connected to a distal end of the control module, and an alternately expandable and closable cauterization loop 24 at the distal tip of the flexible tubular member 22. A flexible sheet or web 26 specifically in the form of a net is attached to cauterization loop 24 for defining a capture pocket. Loop 24 defines the mouth of the capture pocket.

Control module 20 comprises a body member or frame 28 which includes a pair of parallel rails 30*a* and 30*b* to which a slider member 32 is reciprocatably secured. Frame 28 has a thumb hole 31 at a proximal end, whereas slider member 32 has a pair of finger holes 34*a* and 34*b* and is fastened to the proximal end of a wire 36 which passes through tubular member 22 and is in turn connected to cauterization loop 24 at the distal end of tubular member 22. Wire 36 is sufficiently flexible to bend with tubular member 22 during the negotiation thereby of curves or bends in a colon during surgery.

Slider member 32 is also provided with an electrical connector 38 which is couplable to a source of electrical energy. During a severing step of a cauterization operation, described in detail hereinafter with reference to FIG. 2E, electrical energy is fed to loop 24 via connector 38 and wire 36.

Capture web 26 is thin and flexible and preferably made of biologically inert flexible transparent synthetic resin or polymeric material such as polyethylene or nylon. Prior to the beginning of a snare cauterization operation, web 26 is disposed in a closed, folded or contracted state, together with loop 24, in the distal end of tubular member 22, as illustrated in FIG. 1B. Concomitantly, slider member 32 is retracted to the proximal end of rails 30*a* and 30*b* (towards the right side of frame 28 in FIG. 1A). Tubular member 22 is inserted in a biopsy channel 40 of an endoscope 42, as shown in FIG. 2A, and the endoscope is inserted into a body cavity of a patient, such as a colon C.

As illustrated further in FIG. 2A, endoscope 42 is conventionally provided at its distal end with a pair of apertures 44 and 46 for respectively delivering light to and receiving light from a surgical site.

Upon the discovery of a polyp P within colon C via the use of endoscope 42, the snare cauterization instrument assembly is shifted in a distal direction so that tubular member 22 protrudes from the distal end of biopsy channel 40. Then, slider member 32 is shifted in a distal direction to eject loop 24 and capture web 26 from tubular member 22. Upon ejection, loop 24 and capture web 26 expand from a contracted or closed configuration into an at least partially opened configuration, as shown in FIG. 2A.

Figure 2B:
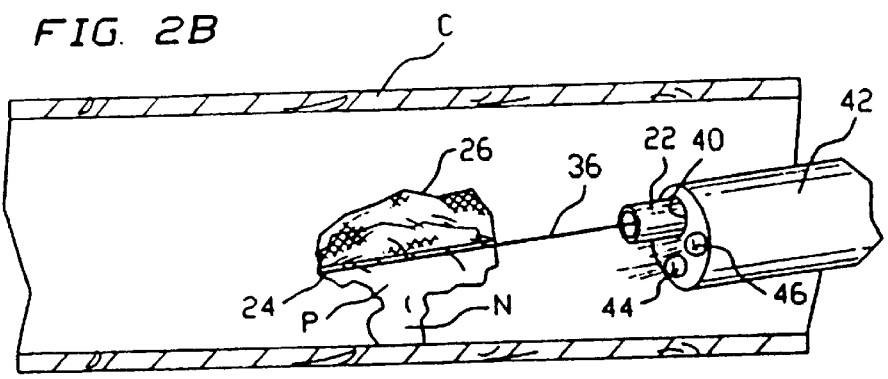
FIG. 2B is a schematic partial cross sectional view similar to FIG. 2A, showing a loop of the snare cauterization instrument assembly of FIG. 1A being passed around the polyp of FIG. 2A.
Figure 2C:
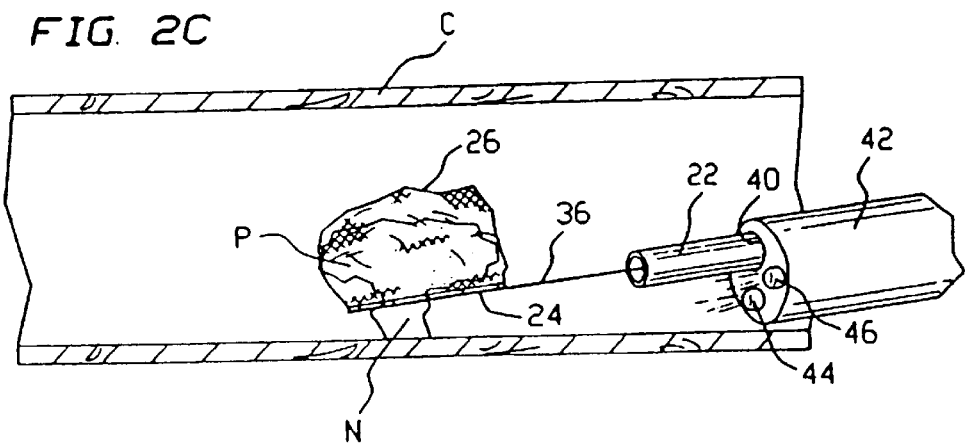
FIG. 2C is a schematic partial cross sectional view similar to FIGS. 2A–2B, showing the loop of the snare cauterization instrument assembly of FIG. 1A completely passed around the polyp of FIG. 2A.

FIG. 2B depicts a later stage in the cauterization procedure. The snare cauterization instrument assembly of FIG. 1A is manipulated to pass loop 24 around polyp P, with capture web 26 following. Eventually, loop 24 encircles a base region or neck N of polyp P and the polyp is surrounded by capture web 26, as shown in FIG. 2C.

Figure 2D:
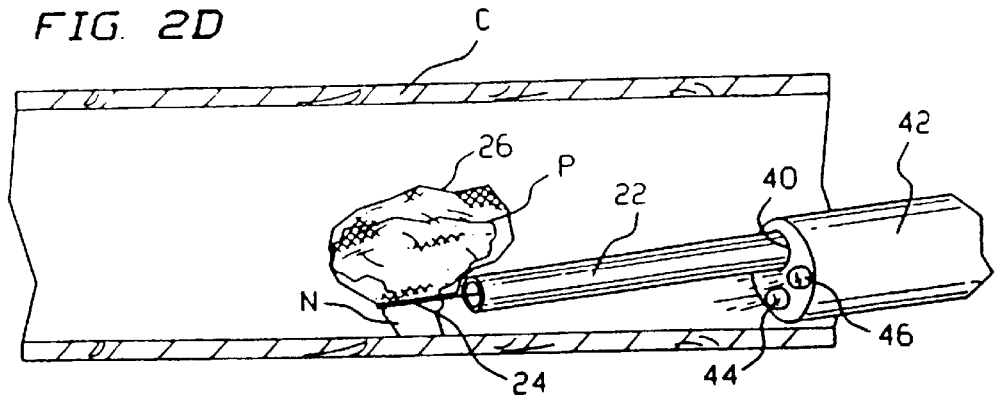
FIG. 2D is a schematic partial cross sectional view similar to FIGS. 2A–2C, showing the loop of the snare cauterization instrument assembly of FIG. 1A being tightened around a base or neck of the polyp.

At that juncture, slider member 32 is pulled back in the proximal direction, whereby wire 36 pulls loop 24 partially back into the distal end of tubular member 22, thereby causing loop 24 to tighten about neck N of polyp P, as illustrated in FIG. 2D.

Figure 2E:
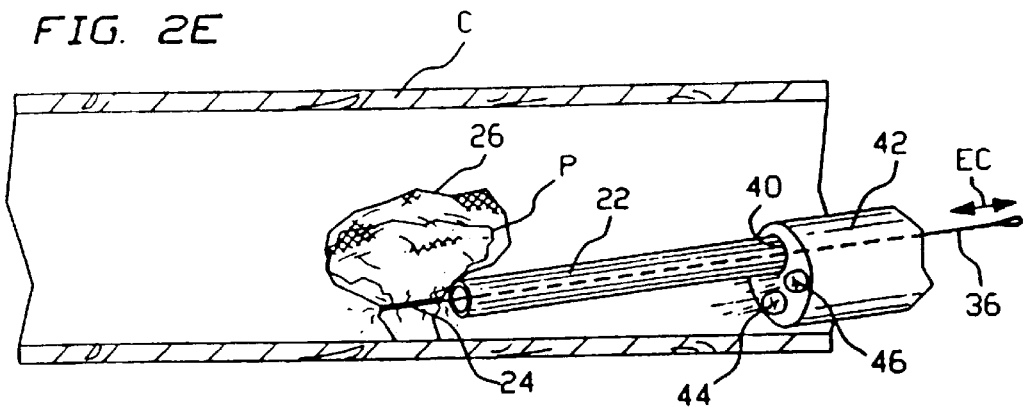
FIG. 2E is a schematic partial cross sectional view similar to FIGS. 2A–2D, showing the loop of the snare cauterization instrument assembly of FIG. 1A in an electrically energized state for burning through the base or neck of the polyp.
Figure 2F:
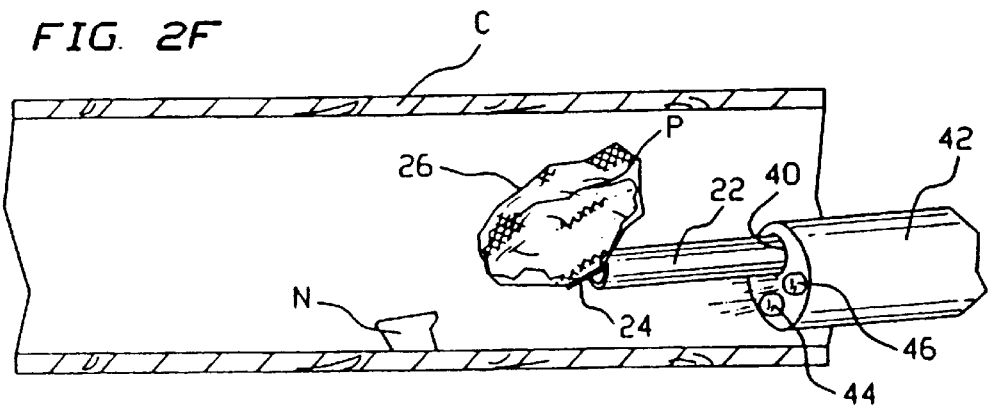
FIG. 2F is a schematic partial cross sectional view similar to FIGS. 2A–2E, showing the polyp severed from the colon wall and captured with the snare cauterization instrument assembly of FIG. 1A.
Figure 2G:
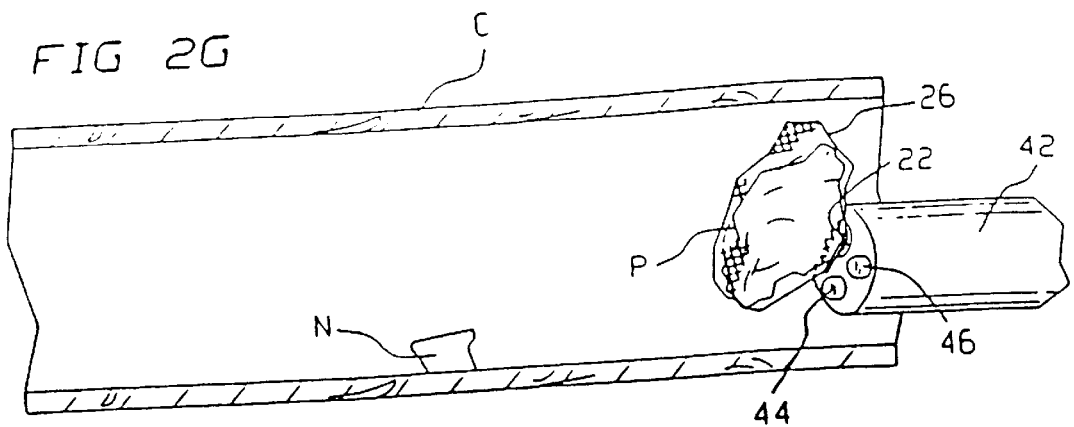
FIG. 2G is a schematic partial cross sectional view similar to FIGS. 2A–2F, showing the snare cauterization instrument assembly of FIG. 1A together with the captured polyp drawn towards the distal end of the endoscope.

As indicated in FIG. 2E, electrical current EC is then caused to pass through wire 36 and loop 24. Generally, electric current from loop 24 is conducted through neck N of polyp P, thereby generating in the polyp tissues heat sufficiently great to sever and cauterize neck N. Upon the severing of polyp P at neck N, slider member 32 is pulled farther in the proximal direction, thereby pulling loop 24 further into the distal end of tubular member 22, as shown in FIG. 2F, to essentially close the loop. Polyp P is now securely trapped in capture web 26. In a further step, depicted in FIG. 2G, the entire snare cauterization instrument assembly including, in particular, tubular member 22, is shifted in the proximal direction relative to endoscope 42. However, care is taken not to draw the distal end of tubular member 22 and particularly capture web 26 with polyp P back into biopsy channel 40 of the endoscope. Polyp P remains in web or capture pocket 26 outside of tubular member 22 and endoscope 42 during the withdrawal of endoscope 42 from the patient.

Every polyp severed by a snare cauterization instrument as described and illustrated herein is captured immediately. Thus, the time for the capture and retrieval of severed polyps is reduced to a minimum. Trauma to patient is likewise reduced, as are hospitalization expenses.

Figure 3:
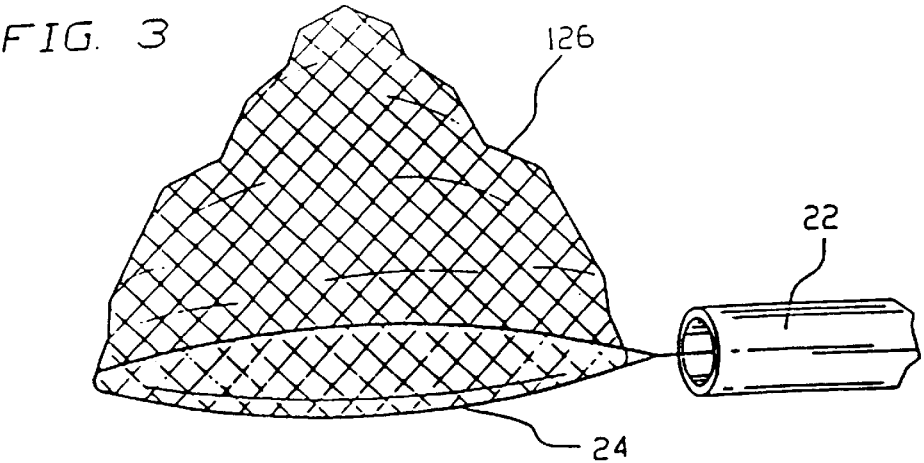
FIGS. 3–6 are schematic partial side perspective views, showing different specific embodiments of a snare cauterization instrument assembly.
Figure 4:
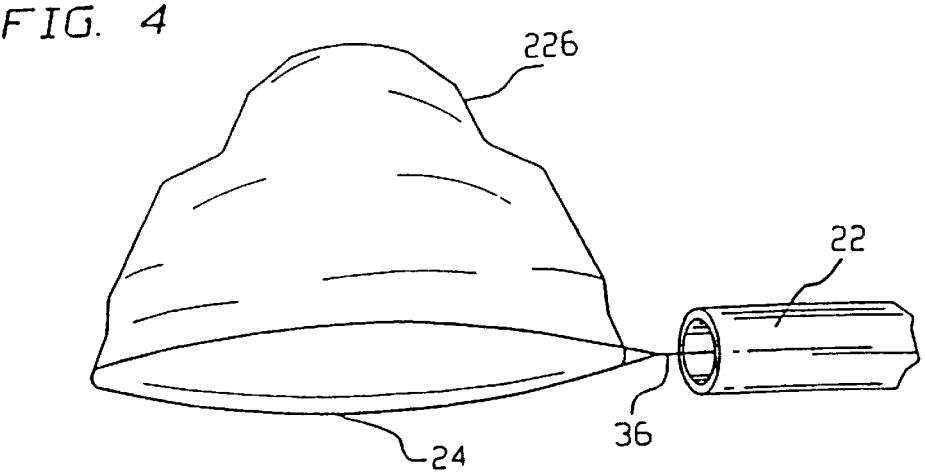
Figure 5:
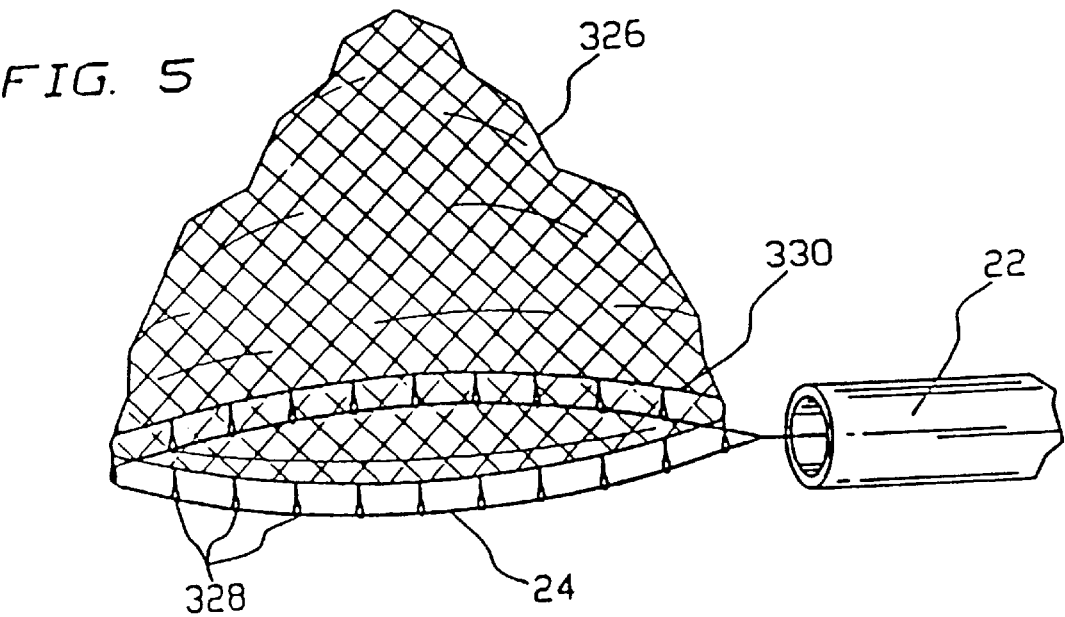
Figure 6:
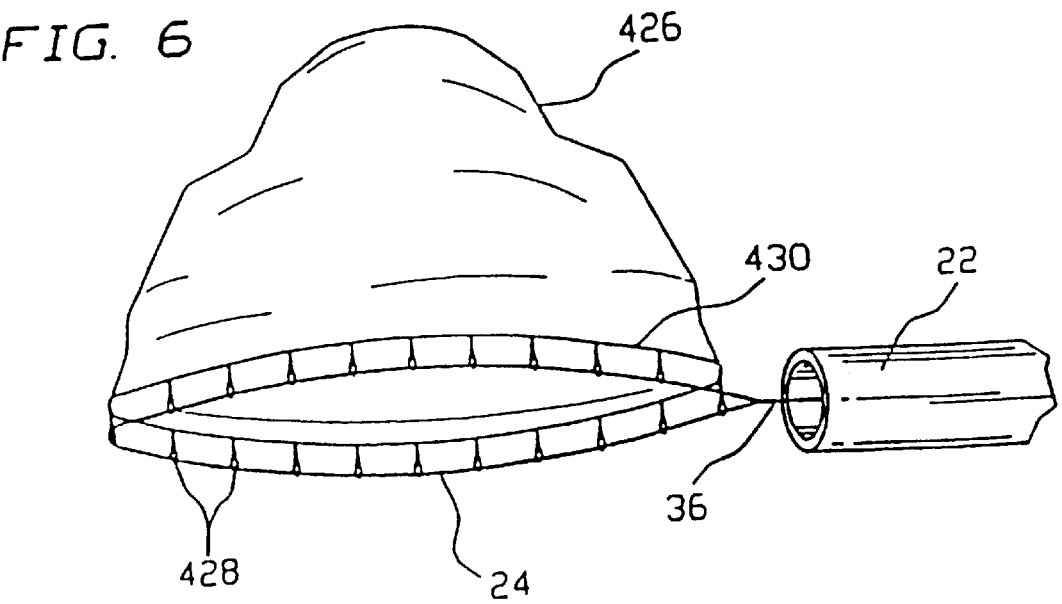

In FIGS. 3–6, like structural components bear the same reference designations. FIG. 3 shows a capture web 126 in the form of a net fastened directly to loop 24, while FIG. 4 shows a capture web 226 in the form of a continuous or solid transparent film fastened directly to loop 24. FIG. 5 illustrates a capture web 326 in the form of a net attached to loop 24 via a multiplicity of spaced ringlets 328. Loop 24 passes through ringlets 328, which are connected to a ring-shaped rim element 330 of web 326. Ringlets 328 are preferably made of a metallic material to facilitate the transmission of electrical current from cauterization loop 24 to the tissues of a polyp. FIG. 6 shows a capture web 426 in the form of a continuous or solid film of transparent polymeric material attached to loop 24 via a multiplicity of spaced ringlets 428. Loop 24 passes through ringlets 428, which are connected to a ring-shaped rim element 430 of web 426.

Figure 7:
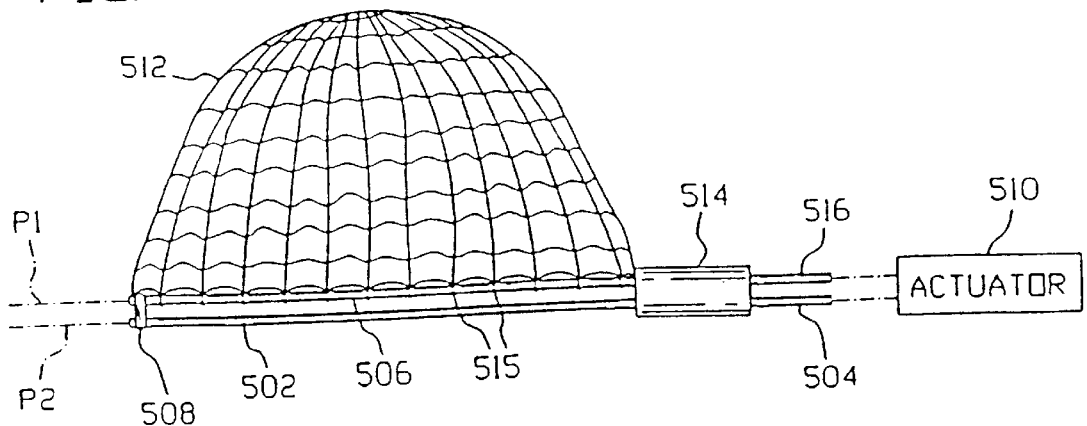
FIG. 7 is a schematic side elevational view, on an enlarged scale, of another embodiment of a snare cauterization instrument assembly, showing a pocket-defining web member on an auxiliary loop.

As illustrated in FIG. 7, a snare cauterization instrument assembly comprises a flexible cauterization loop 502, an electrical conductor 504 operatively connected to the cauterization loop for feeding an electrical current thereto, and a flexible auxiliary loop 506 connected via a fastening element 508 to the cauterization loop only at a distal end thereof. An actuator 510 is operatively connected to cauterization loop 502 and auxiliary loop 506 for alternately expanding and contracting the two loops in tandem with one another. A flexible web member 512 in the form of a net (or a continuous transparent membrane) is connected to auxiliary loop 506 essentially around the circumference thereof to form a capture pocket, auxiliary loop 506 defining a mouth opening of the pocket. Preferably, net 512 is fixed to auxiliary loop 506 only at a distal end and a proximal end (inside a tubular sheath member 514) thereof, the remaining connections 515 being slidable.

Actuator 510 is connected to cauterization loop 502 via conductor 504, which functions in response to manipulations of actuator 510 to eject cauterization loop 502 from a collapsed storage position inside the distal end of tubular sheath member 514 and subsequently to pull cauterization loop 502 back into the sheath member. Actuator 510 is coupled to auxiliary loop 506 via a flexible wire or rod member 516 which like conductor 504 extends longitudinally through sheath member 514.

Figure 8:
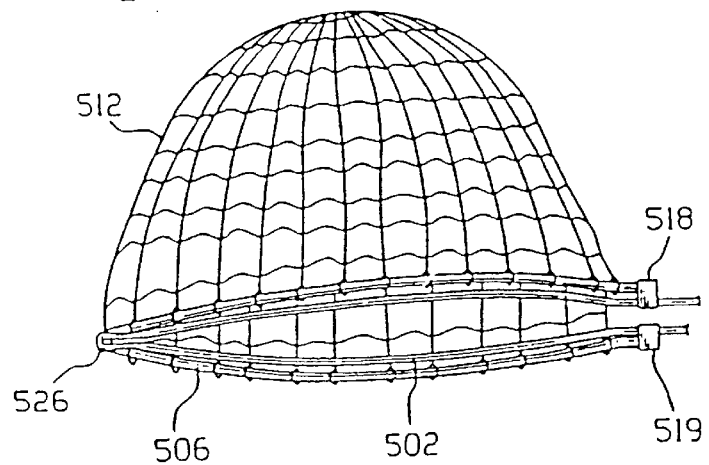
FIG. 8 is a schematic perspective view, also on an enlarged scale, of a modified snare cauterization instrument assembly, showing an auxiliary loop attached at three points to a cauterization loop.

Cauterization loop 502 and auxiliary loop 506 are disposed in parallel planes P2 and P1, respectively. As depicted in FIG. 8, auxiliary loop 506 may be connected at a proximal end to cauterization loop 502 at two points 518 and 519, as well as to the distal end of the cauterization loop. In that event, wire or rod member 516 may be omitted. As further shown in FIG. 8, auxiliary loop 506 is slightly larger than cauterization loop 502. The loops 502 and 506 are close, almost touching one another. As described above with reference to FIG. 7, web member 512 is fixedly connected to auxiliary loop 506 at a distal end and a proximal end thereof and slidably connected to the auxiliary loop between those ends.

FIG. 9 shows a cauterization loop 520 and an auxiliary loop 522 connected to one another at a distal end via a fastener 524. Cauterization loop 520 and auxiliary loop 522 are essentially coplanar in the expanded configuration illustrated in FIG. 9. During an ejection stroke and a subsequent retraction stroke of cauterization loop 520 and auxiliary loop 522 in response to the manipulations of an actuator (not shown) at a proximal end (not shown) of the instrument assembly, cauterization loop 520 and auxiliary loop 522 expand and contract in unison in essentially a common plane.

The embodiments of a cauterization snare instrument assembly illustrated in FIGS. 7–9 are less expensive to manufacture than the ringlet embodiments of FIG. 5 and 6 and enable use of a wider range of materials for the pocket or web member (512 in FIG. 7) than the embodiments of FIGS. 3 and 4. In addition, a primary advantage of the particular dual loop embodiments of FIGS. 7–9 is that auxiliary loops 506 and 522 are not connected to the cauterization loops 502 and 520 along operative portions thereof, thereby eliminating any possible interference that the auxiliary loops or capture nets 512 and 523 (FIG. 9) might otherwise exhibit with respect to the cutting and cauterization operations.

As illustrated in FIGS. 8 and 9, this elimination of possible interference in the cutting and cauterization operations is furthered by forming cauterization loops 502 and 520 at their distal ends with respective tongue-like extensions 526 and 528 to which auxiliary loops 506 and 522 are connected. Extensions 526 and 528 may be coated with an insulating material (not illustrated) and serve to separate fasteners 508 and 524 from the site of the cauterization procedure.

Auxiliary loops 506 and 522 are made of electrically nonconductive material preferably in the form of a synthetic resin or polymeric material such as polyethylene or nylon.

In using the snare cauterization instrument assemblies of FIGS. 7–9, cauterization loop 502 or 520 and auxiliary loop 506 or 522 are expanded from a collapsed configuration inside the distal end of sheath member 514 to an expanded configuration. In the expanded configuration, auxiliary loop 506 or 522 is preferably larger than cauterization loop 502 or 520 and essentially parallel thereto. A special case of parallelism is found where the cauterization loop and the auxiliary loop are coplanar.

Pursuant to additional steps in the procedure, pocket or web member 512 or 523 is opened during the expansion of cauterization loop 502 or 520 and auxiliary loop 506 or 522 and the expanded loops are passed over a selected polyp or other internal tissue agglomeration to be removed, so that web member 512 or 523 substantially surrounds the polyp. Cauterization loop 502 or 520 is then closed by pulling it into the distal end of sheath member 514 or 525 (FIG. 9). The closure of cauterization loop 502 or 520 around a base region of the polyp while the cauterization loop is energized with electrical current serves to severe the polyp at its base. Maintaining web member 512 or 523 surrounding the polyp during the cauterization procedure serves to capture the severed polyp at the instant of its severance.

As illustrated in FIG. 10, a modified snare cauterization assembly includes a cauterization loop 530 surrounded along a substantial portion of its length by a tubular jacket or sleeve 532 to which a flexible pocket-defining web member 534 is connected. Jacket or sleeve 532 is made of a heat-conductive and electricity-conductive material enabling cauterization to proceed through the medium of the sleeve. In addition, sleeve 532 is provided with a coating or layer 535 of a biocompatible dye or ink material of a predetermined color. Color from coating 535 is transferred from the cauterization loop and particularly from sleeve 532 during the conduction of current through the loop. Coating 535 may be a liquifiable solid or a powder. Such a color-transferable coating or layer may be provided directly on any of the cauterization loops described herein. The deposition of a common color on a severed polyp and an unsevered neck or base area serves to facilitate a locating of the polyp's original situs upon a subsequent identification of the polyp as being malignant or a carcinoma. This is especially advantageous where several polyps are caught in the same procedure (see FIG. 15).

As illustrated in FIG. 11, another modified snare cauterization assembly comprises a cauterization loop 536 enclosed along essentially its entire length by a tubular jacket or sleeve 538 to which a flexible pocket-defining web member 540 is coupled. Sleeve 538 is provided along an inner side with a plurality of longitudinally extending windows 542 for facilitating or enabling the conduction of heat and/or electrical current from cauterization loop 536 to organic tissues of a polyp or other cell mass to be removed from a patient's body.

Figure 12:
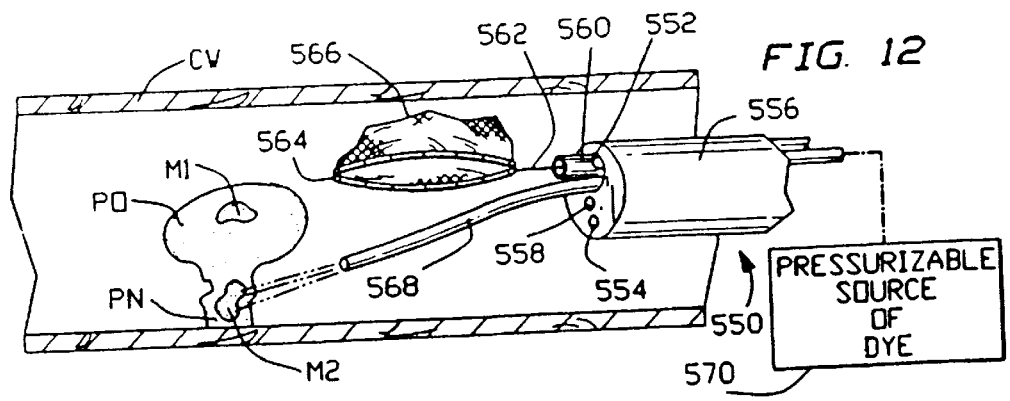
FIG. 12 is a schematic partial cross sectional view of a patient's colon with a polyp, showing a snare cauterization instrument assembly inserted through the biopsy channel of an endoscope which is itself inserted into the patient's colon, and further showing an instrument for depositing color markers on organic tissues.

As shown in FIG. 12, a surgical instrument assembly for use in a snare cauterization operation comprises an endoscope assembly 550 including a biopsy channel 552 and a light outlet 554 at a distal end of an endoscope insertion member 556 for delivering light to a surgical site inside a patient. The distal end of the endoscope insertion member 556 is further provided with a light inlet 558 for receiving light reflected from a surgical site. Light outlet 554 and light inlet 558 are located at the distal ends of a fiber optic illumination guide (not shown) and a fiber optic image guide (not shown), respectively, which extend longitudinally through endoscope insertion member 556.

As further illustrated in FIG. 12, a tubular sheath member 560 is inserted through biopsy channel 552, while a metal wire 562 passes longitudinally through the sheath 560 and is operatively connected at a distal end to an alternately expandable and collapsible metallic cauterization loop 564. An electrical supply (not shown in FIG. 12) is operatively connected to wire 562 for feeding an electrical current to loop 564 via the wire. A manually actuatable shifter (not illustrated in FIG. 12) is operatively connected to wire 562 at a proximal end thereof for longitudinally sliding the wire along sheath 560 in alternately opposite directions. A flexible web member 566 is connected to loop 564 to form a capture pocket, the loop defining a mouth opening of the pocket. Web member 566 is attached to loop 564 in a manner so as to expose the loop to enable effective cauterization of organic tissues by the loop.

Also extending through biopsy channel 552 is a tubular member 568 connected at a proximal end to a pressurizable dye or color source 570 such as a hypodermic syringe filled with a biocompatible liquid of a predetermined hue. A distal end portion of tubular member 568 is ejected from biopsy channel 552 upon arrival of the distal end of endoscope assembly 550 at an internal surgical site where a polyp PO is detected via light outlet 554 and light inlet 558 of endoscope assembly 550. Colored fluid is squirted from tubular member 568 to place recognizable markers M1 and M2 on polyp PO and a lower portion of a polyp neck PN by which polyp PO is connected to a colon wall CW of a patient. Markers M1 and M2 enable subsequent identification of the original location of polyp PO upon a medical analysis of the polyp after it has been severed and removed from the patient in accordance with procedures described herein and other steps known to those skilled in the art.

Upon an insertion of endoscope insertion member 556 into a patient's colon, endoscope assembly 550 is used to visually monitor internal body tissues of the patient, including the internal surface of colon wall CW. Upon detecting selected internal body tissues (e.g., polyp PO) to be removed from the patient, loop 564 and web member 566 are ejected from a distal end of biopsy channel 552. Loop 564 and web member 566 are at least partially expanded from a collapsed configuration upon their ejection from biopsy channel 552. Loop 564 is manipulated from outside of the patient, e.g., via endoscope assembly 550 and more particularly via wire 562 or sheath 560, to pass the expanded loop over the polyp PO so that web member 566 substantially surrounds the polyp. Subsequently, loop 564 is closed to engage the polyp PO around a base region thereof. Closure is effectuated by sliding sheath 560 in a distal direction so that a proximal part of loop 564 is retracted into the sheath. An electrical current is conducted through the closed or partially closed loop 564 to burn through the base region of polyp PO, thereby severing the polyp PO at the base region. Loop 564 is closed further upon a completed burning of the loop through the base of the polyp PO, thereby capturing the severed polyp in web member or pocket 566.

Polyp PO and neck PN may be marked with a biocompatible dye or ink by tubular member 568 prior to the cauterization procedure. Alternatively, at least the neck portion PN may be marked after polyp PO has been severed by loop 564 and captured in web member 566. Tubular member 568 operates to spray a determinable quantity of liquid dye or ink onto the surfaces of polyp PO and neck or base PN.

Figure 13:
FIG. 13 is partially a schematic partial side elevational view and partially a block diagram of another color deposition instrument alternatively utilizable with the endoscopic snare cauterization instrument assembly of FIG. 12.

As illustrated in FIG. 13, another instrument 572 utilizable with endoscope assembly 550 to mark organic tissues inside a patient comprises a tubular member 574 operatively connected at a proximal end to a pressurized or pressurizable supply 576 of a biocompatible fluidic dye material. At a distal end, tubular member 574 is provided with a needle 578 for use in injecting the dye material below the surface of polyp PO and neck PN.

Figure 14:
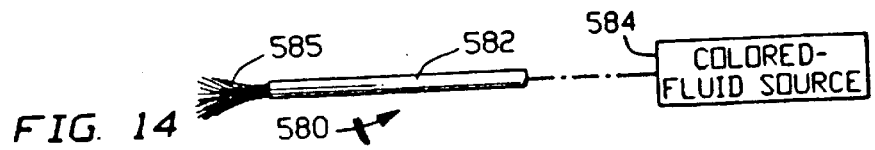
FIG. 14 is partially a schematic partial side elevational view and partially a block diagram of yet another color deposition instrument alternatively utilizable with the endoscopic snare cauterization instrument assembly of FIG. 12.

As shown in FIG. 14, another instrument 580 utilizable with endoscope assembly 550 to mark organic tissues inside a patient comprises a tubular member 582 operatively connected at a proximal end to a pressurized or pressurizable supply 584 of a biocompatible fluidic dye material. At a distal end, tubular member 582 is provided with a brush 585 for use in applying or painting the dye material on the surface of polyp PO and neck PN.

Figure 15:
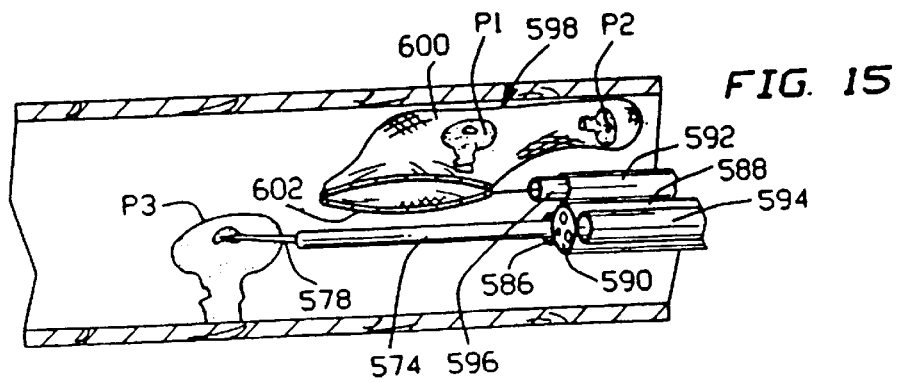
FIG. 15 is a schematic partial cross sectional view of a patient's colon with a polyp, showing a snare cauterization instrument assembly inserted through an alternately collapsible and expandable biopsy channel of an endoscope assembly which is itself inserted into the patient's colon, and further showing an instrument for depositing color markers on organic tissues.

Instrument 572 of FIG. 13 or instrument 580 of FIG. 14 may be inserted through biopsy channel 552 of endoscope assembly 550. Alternatively, tubular member 568 or marking instrument 572 or 580 may be inserted through an alternately expandable and collapsible biopsy channel 586 provided on a sheath 588 surrounding an endoscope insertion member 590, as illustrated in FIG. 15. Such an endoscope sheath 588 may take the form described and illustrated in U.S. Pat. Nos. 4,646,722 and 5,025,778, the disclosures of which are hereby incorporated by reference.

Sheath 588 is provided with other alternately expandable and collapsible biopsy channels 592 and 594, one of which receives a sheath 596 of a cauterization instrument assembly 598. As depicted in FIG. 15, an expanded web member 600 at a distal end of instrument assembly 598 carries a pair of polyps P1 and P2 which have already been marked with respective colors and severed. FIG. 15 shows a third polyp P3 being marked by instrument 572 (FIG. 13) prior to cauterization and severing by a loop 602 to which web member 600 is attached in a manner to enable cauterization by the loop.

Figure 16:
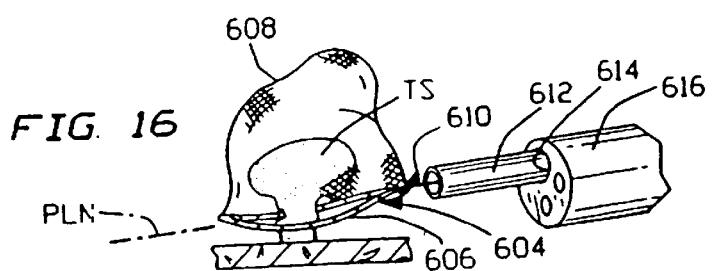
FIG. 16 is a schematic perspective view of a distal end portion of an endoscopic cauterization instrument assembly, showing a cauterization loop of the assembly in use to cauterize and sever a polyp in a patient's colon.

As shown in FIG. 16, another assembly for use in severing and removing an organic tissue sample TS from inside a patient comprises a cauterization loop 604 which in an expanded configuration has a bent configuration which arcs at 606 laterally from a plane PLN in which the loop opens and closes. Arc or curvature 606, inherent in the prestressed or spring-biased construction of loop 604, facilitates the capture of polyps by facilitating the encirclement thereof, as indicated in FIG. 16. The curved design of FIG. 16 may be used in any of the snare embodiments described herein, as well as in prior art cauterization loops without an attached capture pocket or web. Loop 604 is provided with a capture pocket 608 and is operatively connected to an electrical energy source (not shown) via an elongate wire 610 extending longitudinally through a sheath 612 in turn extending through a biopsy channel 614 of an endoscope insertion member 616.

It is to be noted that colored staples may be used to mark a polyp and/or its base, the staples being applied via an endoscopic stapling instrument as disclosed in U.S. Pat. Nos. 5,015,249 and 5,049,153 and 5,156,609, the disclosures of which are hereby incorporated by reference. The staples may be applied to the base or neck of a severed polyp either before or after a cauterization procedure.

Figure 17A:
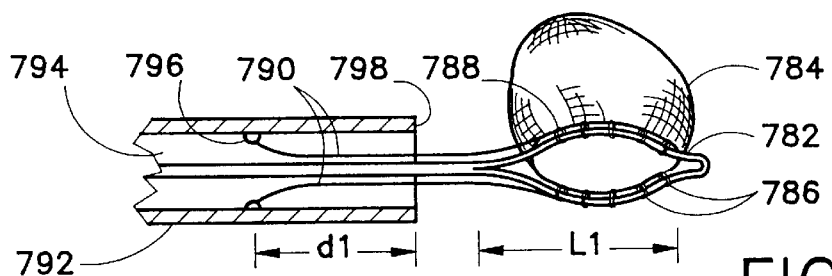
FIGS. 17A–17C are schematic side perspective views, partially in cross-section, of another modified cauterization snare and capture pocket, showing three steps in the use of the device.
Figure 17B:
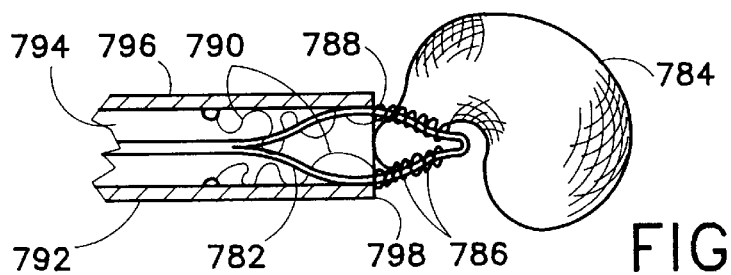
Figure 17C:
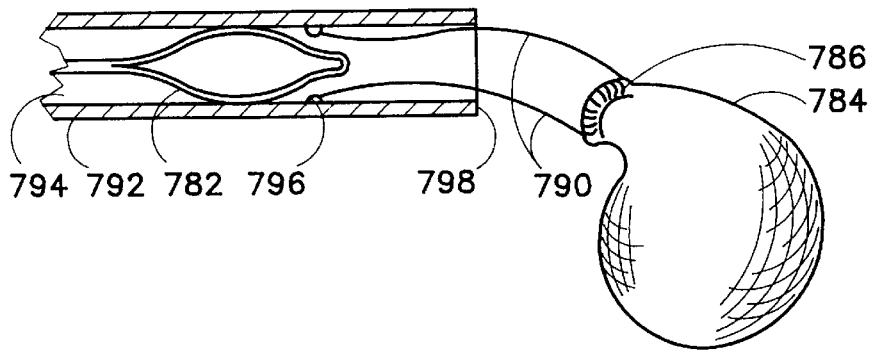

FIGS. 17A–17C illustrate steps in using a modified snare including a cauterization loop 782 with a capture pocket 784 attached by burnable ringlets 786 to the loop. The two most proximal ringlets 788 are connected via respective threads 790 to an inner surface or side 794 of a deployment sheath 792. Points of connection 796 of threads 790 to sheath surface 794 are located at a distance d1 from the distal tip 798 of sheath 792 approximately equal to half of the length L1 of loop 782.

Upon an extension of loop 782 from sheath 792, as illustrated in FIG. 17A, threads 790 pull ringlets 788 in a proximal direction to the proximal side of loop 782, thereby stretching capture pocket 784 out to an optimally opened configuration. Of course, threads 790 also limit the extent to which loop 782 may be distanced from the distal end of sheath 792.

FIG. 17B shows the sliding of ringlets 786 and 788 in a distal direction relative to loop 782 upon a retraction of the loop into sheath 792, after loop 782 and pocket 784 have been placed about a polyp (not shown). In the event that the user endoscopist decides that an adjustment of the snare relative to the polyp is desired, loop 782 is pushed in a distal direction relative to sheath 792. This movement may be accomplished, of course, by pulling sheath 792 in a proximal direction relative to loop 782. Upon a sufficient ejection of loop 782 from sheath 792, threads 790 again pull ringlets 788 in a proximal direction to the proximal side of loop 782 to thereby open capture pocket 784.

If the user endoscopist decides that loop 782 is propitiously positioned relative to the subject polyp, loop 782 is pulled further into sheath 792, as illustrated in FIG. 17C. Ringlets 786 and 788 are severed from loop 782 via a burning process, thereby freeing capture pocket 784 from loop 782. The polyp cauterization assembly of FIGS. 17A–17C may be provided with a purse string for ensuring closure of capture pocket 784 upon completion of a polyp severing operation.

Figure 18:
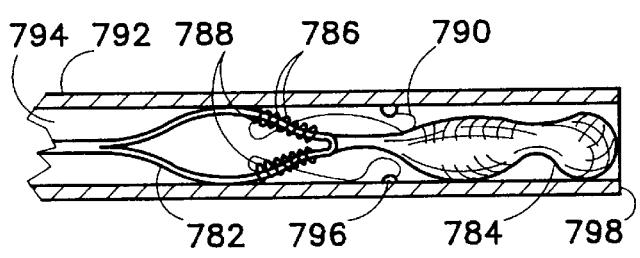
FIG. 18 is a schematic side elevational view, partially in cross-section, showing the cauterization snare and capture pocket of FIGS. 17A–17C in a retracted pre-firing insertion configuration.

As shown in FIG. 18, in packing loop 782 and pocket 784 inside sheath 792, pocket 784 may be disposed distally of loop 782, thereby facilitating the packaging process.

Figure 19:
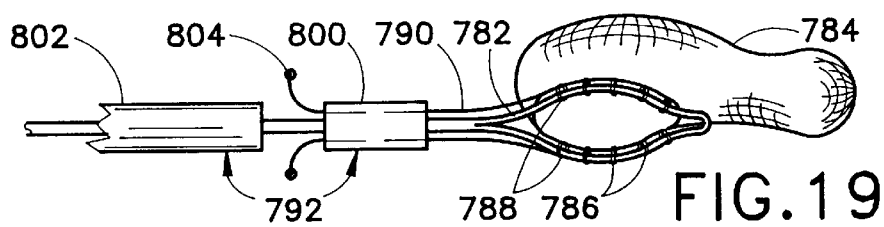
FIG. 19 is a schematic side elevation view showing a stage in the assembly of the cauterization snare and capture pocket of FIGS. 17A–17C and 18.

FIG. 19 illustrates a step in a manufacturing operation. Sheath 792 includes a distal segment 800 which is attached to a body portion 802 of the sheath via ultrasonic welding, adhesive, heating, or other process. Threads 790 extend through segment 800 and are sandwiched between segment 800 and body portion 802 upon connection of those sheath elements to one another. Threads 790 may be provided additionally with knots 804 which are located outside of the sheath 792 upon completion of manufacturing. Knots 804 serve as anchors, preventing dislodgement of threads 790 during use of the cauterization snare assembly.

Figure 20:
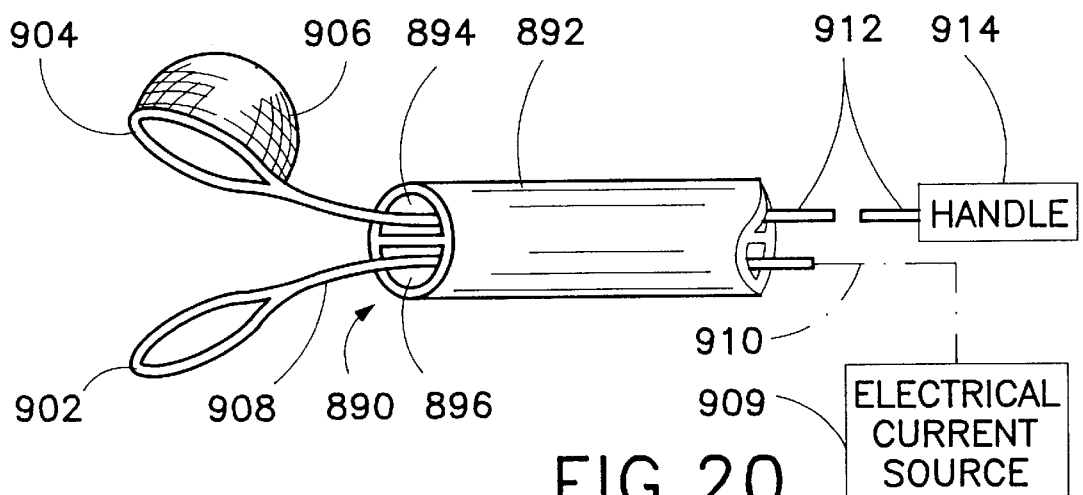
FIG. 20 is a schematic side perspective view, on an enlarged scale, of an endoscopic surgical instrument assembly.

As illustrated in FIG. 20, a surgical instrument assembly 890 for use in snare cauterization operations comprises a tubular instrument guide member 892 defining a plurality of separate longitudinally extending lumens 894 and 896. Lumens 894 and 896 have semi-circular cross-sections. Tubular member 892 has a diameter sufficiently small so that the tubular member can be inserted through a biopsy channel 898 of a flexible endoscope insertion member 900 (FIGS. 21A–21E). Instrument assembly 890 further comprises a cauterization loop 902 and an auxiliary loop 904 which is provided with a flexible web member 906 defining an alternately expandable and contractible capture pocket. Auxiliary loop 904 defines a mouth opening of the pocket.

Figure 21A:
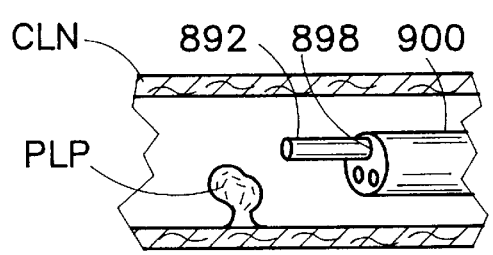
FIGS. 21A–21E are partially schematic cross-sectional views of a colon and partially schematic side perspective views of an endoscope incorporating the instrument assembly of FIG. 20 showing successive steps in the performance of an endoscopic operation.

An electrically conductive wire 908 is connected to cauterization loop 902, cauterization loop 902 and wire 908 being disposed at least partially in lumen 896 of tubular member 892. An electrical supply 909 is operatively connected to wire 908 via a coupling 910 for feeding an electrical current to cauterization loop 902 via wire 908. An elongate flexible shifting member 912 (e.g., a wire) is connected at one end to auxiliary loop 904. Auxiliary loop 904 and wire 912 are at least partially disposed in lumen 894 of tubular member 892. A handle assembly 914 is provided at the proximal end of wire 912 for facilitating the maneuvering of auxiliary loop 904 from outside the patient. Handle assembly 914 may also be connected to cauterization loop 902 to facilitate the manipulation of the loop to eject the loop from lumen 896 and to place the loop about a polyp PLP (FIG. 21A). Handle assembly 914 is operatively connected to cauterization loop 902 and auxiliary loop 904 so as to allow those two elements to be ejected independently from tubular member or catheter 892.

Web member 906, whether a net or a continuous film of polymeric material, may be connected to auxiliary loop 904 at a plurality of spaced locations, e.g., via ringlets (not shown). Tubular member 892 is preferably flexible so that it may pass along bends in endoscope insertion member 900 upon a deployment thereof during an endoscopic investigation.

As depicted in FIG. 21A, upon introduction of endoscope insertion member 900 into a patient's colon CLN and use of the endoscope assembly to visually monitor internal body tissues of the patient to locate polyp PLP, tubular member 892 is moved in a distal direction through biopsy channel 898 of endoscope insertion member 900 to eject a distal end portion of the tubular member from the biopsy channel.

Figure 21B:
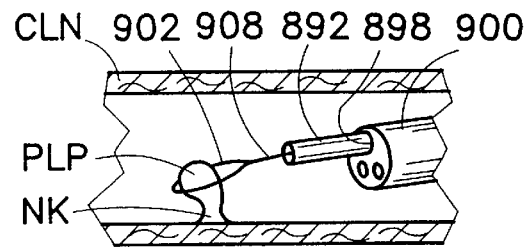

Subsequent steps of an endoscopic surgical procedure are depicted in FIG. 21B. Cauterization loop 902 is shifted in a distal direction relative to ejected tubular member 892 to eject the cauterization loop from the tubular member. Upon ejection, ejected cauterization loop 902 is expanded from a collapsed configuration inside tubular member 892 to an opened configuration. Cauterization loop 902 is then manipulated from outside of the patient to pass the expanded cauterization loop over polyp PLP which is to be removed from the patient.

Figure 21C:
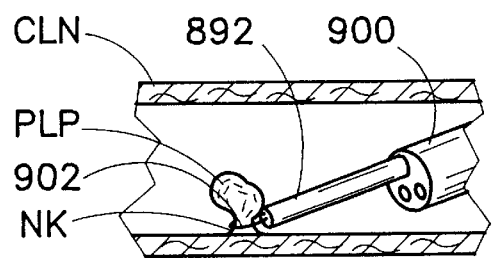

As illustrated in FIG. 21C, cauterization loop 902 is at least partially closed to engage polyp PLP around a base region or neck NK thereof. This closure is effectuated by shifting tubular member 892 and cauterization snare relatively towards one another to thereby at least partially withdraw or retract cauterization loop 902 into tubular member 892. Upon closure of cauterization loop 902 about polyp neck NK, an electrical current is conducted through wire 908 and cauterization loop 902 to burn through polyp PLP at base region or neck NK thereof, thereby severing the polyp at the neck.

Figure 21D:
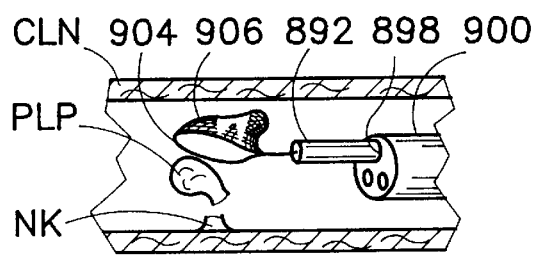
Figure 21E:
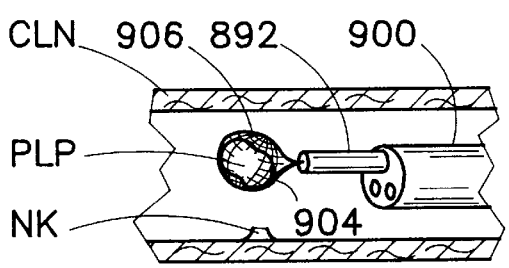

Upon a severing of the polyp PLP at the neck NK, cauterization loop 902 is retracted into tubular member 892. Then, auxiliary loop 904 is ejected from tubular member 892, the auxiliary loop and web member or capture pocket 906 being opened from a folded configuration inside lumen 94 of tubular member 892 to an at least partially expanded or opened configuration, as illustrated in FIG. 21D. Subsequently, auxiliary loop 904 is maneuvered from outside the patient to pass the opened auxiliary loop 904 over the severed polyp PLP so that web member or pocket 906 substantially surrounds the polyp. At that juncture, auxiliary loop 904 is at least partially closed to capture the severed polyp PLP in web member or pocket 906, as shown in FIG. 21E. As further indicated in FIG. 21E, the closing of auxiliary loop 904 includes shifting tubular member 892 and the auxiliary loop relatively towards one another to thereby at least partially withdraw auxiliary loop 904 into tubular member 892. After capture has been effectuated, polyp PLP is removed from the patient together with auxiliary loop 904 and the capture pocket 906. Biopsy channel 898 of endoscope member 900 may be located in a sheath disposed on the endoscope, as described in U.S. Pat. No. 5,217,001, the disclosure of which is hereby incorporated by reference.

It is to be noted that the device or instrument assembly of FIG. 20 includes a cauterization wire disposed simultaneously with a separate capture pocket in a common tubular instrument guide member.

Figure 22A:
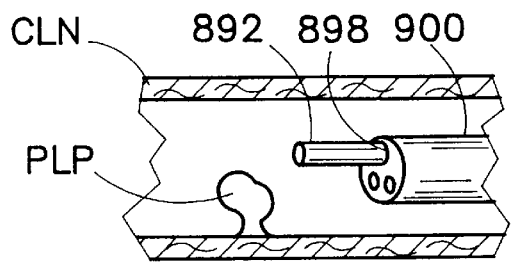
FIGS. 22A–22F are partially schematic cross-sectional views similar generally to FIGS. 21A–21E, showing an alternative series of successive steps in an endoscopic operation.

FIGS. 22A–22E depict a sequence of steps in another endoscopic polyp removal procedure. FIG. 22A is identical to FIG. 21A and shows endoscope insertion member 900 inserted into colon CLN. Insertion member 900 is used to visually monitor internal body tissues of the patient to locate polyp PLP. Upon locating polyp PLP, the endoscopist moves tubular member 892 in a distal direction through biopsy channel 98 of endoscope insertion member 900 to eject the distal end portion of the tubular member from the biopsy channel.

Figure 22B:
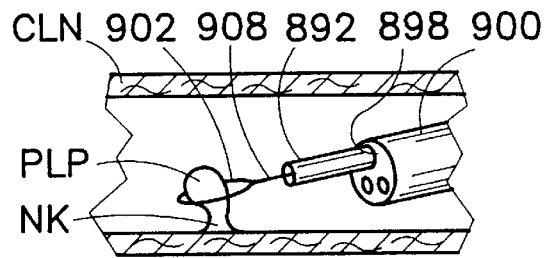

FIG. 22B is identical to FIG. 21B and illustrates subsequent steps of the endoscopic polyp removal procedure. Cauterization loop 902 is shifted in a distal direction relative to ejected tubular member 892 to eject the cauterization loop from the tubular member. Upon ejection, ejected cauterization loop 902 is expanded from a collapsed configuration inside tubular member 892 to an opened configuration. Cauterization loop 902 is then manipulated from outside of the patient to pass the expanded cauterization loop over polyp PLP which is to be removed from the patient.

Figure 22C:
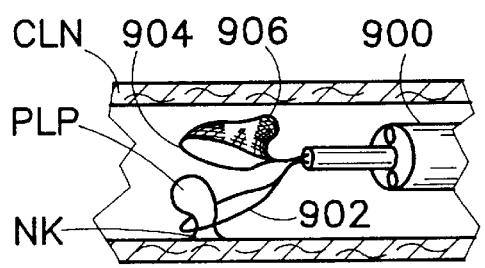
Figure 22D:
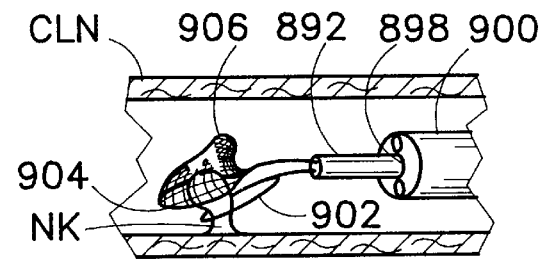
Figure 22E:
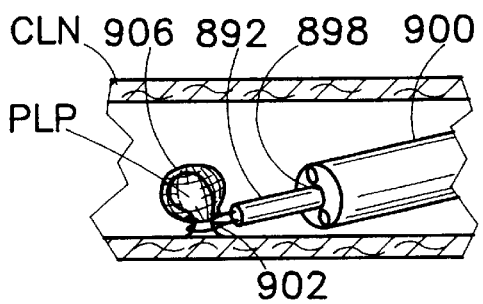

As illustrated in FIG. 22C, cauterization loop 902 is maneuvered to encircle polyp PLP around base region or neck NK thereof. Prior to completing a closure of cauterization loop 902 about polyp PLP, auxiliary loop 904 and capture pocket 906 are ejected from tubular member 892 and are opened from a folded configuration inside lumen 894 of tubular member 892 to an at least partially expanded or opened configuration. As illustrated in FIG. 22D, auxiliary loop 904 is then maneuvered from outside the patient to pass the opened auxiliary loop 904 and capture pocket 906 over the polyp PLP so that web member or pocket 906 substantially surrounds the polyp. At that juncture, tubular member 892 on the one hand and cauterization loop 902 and auxiliary loop 904 on the other hand are shifted relatively towards one another to thereby effectuate a partial closure of the loops about polyp PLP, particularly about neck region NK thereof, as shown in FIG. 22E.

Figure 22F:
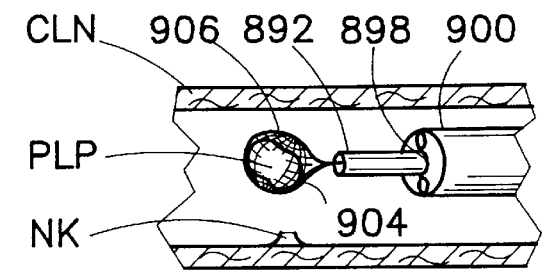

Upon closure of cauterization loop 902 about polyp neck NK, an electrical current is conducted through wire 908 and cauterization loop 902 to bum through polyp PLP at base region or neck NK thereof, thereby severing the polyp at the neck. Simultaneously with the current flow, cauterization loop 902 is drawn into tubular member 892. The severed polyp is automatically or naturally captured within pocket 906, as illustrated in FIG. 22F. After capture has been effectuated, polyp PLP is removed from the patient together with auxiliary loop 904 and the capture pocket 906.

Figure 23:
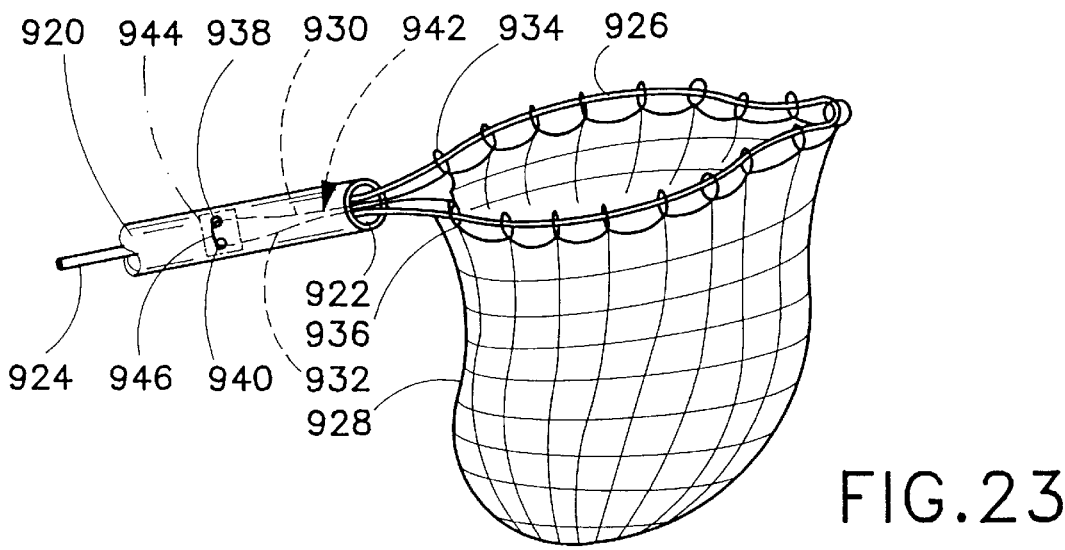
FIG. 23 is a schematic perspective view, on an enlarged scale, of a capture pocket or pouch, showing the capture pocket or pouch in an opened configuration.
Figure 24:
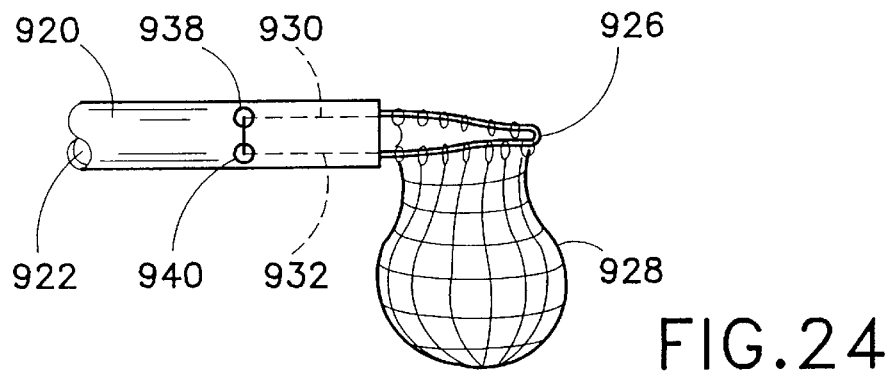
FIG. 24 is a side elevational view of the capture pocket or pouch of FIG. 23, showing the capture pocket or pouch in a substantially closed configuration.

FIGS. 23 and 24 illustrate an improvement in a loop and pouch assembly which may be incorporated into the assembly of FIG. 20. The assembly comprises a tubular member 920 defining at least one longitudinally extending lumen 922. Tubular member 920 has a diameter sufficiently small so that the tubular member can be inserted though a biopsy channel of a flexible endoscope. An elongate flexible shifting member 924 is connected at one end to a flexible loop 926, the loop and the shifting member being at least partially disposable in lumen 922. A flexible web member 928 is connected to loop 926 so as to form a capture pocket or pouch. Loop 926 defines a mouth opening of pocket 928. At least one flexible tensile member or tether 930 and preferably two flexible tensile members 930 and 932 are connected to flexible web member or pocket 928 at proximal end points 934 and 936 thereof. Flexible tensile members 930 and 932 are also connected to tubular member 920 at a pair of holes 938 and 940 formed in tubular member 920 at points spaced from a distal end thereof. Tensile members 930 and 932 extend from flexible web member 928 into lumen 922 of tubular member 920.

Tensile members 930 and 932 are segments of a single flexible tensile tether member 942 which extends through holes 938 and 940 in tubular member 920. A patch 944 is disposed on an outer surface of tubular member 920 over holes 938 and 940 and over a bight portion 946 of tensile member 942 which is located outside the tubular member. Patch 944 is a thin film of polymeric material which is heat shrunk tightly over the tubular member 920. Patch 944 ensures that bight portion 946 of tensile member or thread 942 is not snagged on possible protuberances inside the endoscope channel.

When loop 926 is ejected from tubular member 920, web member or capture pocket 928 slides along loop 926, staying outside of the tubular member, as illustrated in FIG. 24. In the event that the loop 926 is subsequently ejected again from the distal end of tubular member 920, tensile segments 930 and 932 hold the proximal end of capture pocket 928 so that the pocket slides back along the emerging loop 926 to become repositioned along the loop as illustrated in FIG. 23.

Figure 25:
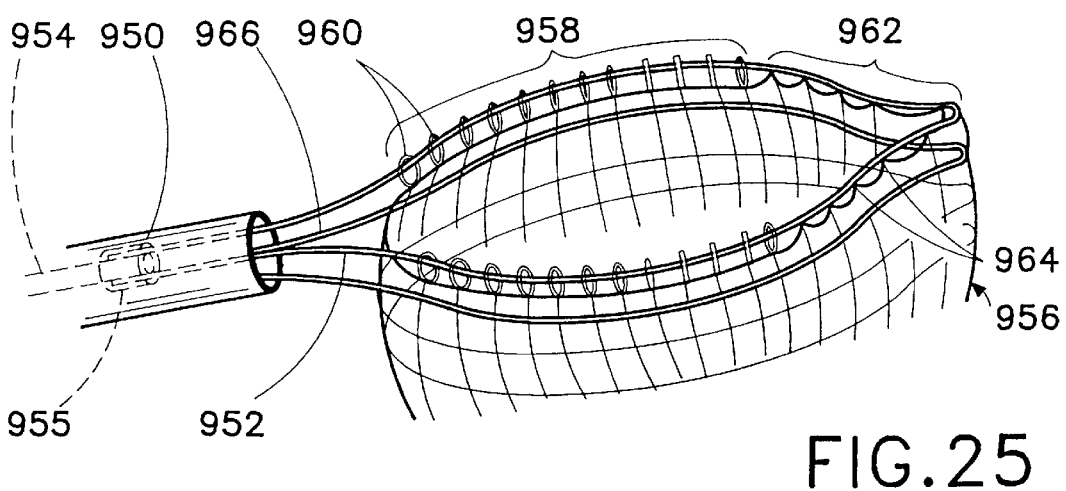
FIG. 25 is a schematic perspective view, on an enlarged scale, of a further capture pocket or pouch, showing the capture pocket or pouch in an opened configuration and attached to a cauterization loop.

The specific embodiment of the invention illustrated in FIGS. 24 and 25 ensures that the pocket 928 can remain outside the tubular member 920 and yet can be reopened or repositioned in the event it is necessary or desirable to eject the loop 926 again. If tensile segments 930 and 932 were attached to loop 926 or shifting member 924, as it is in some prior art pouches, a polyp contained in capture pocket 928 would be mashed owing to a dragging of the pocket and its contents into tubular member 920.

As illustrated in FIG. 25, an endoscopic surgical instrument for use in snare cauterization operations comprises a tubular sheath member 950, an alternately expandable and contractible cauterization loop 952, and an electrically conductive wire 954 operatively connected to the loop. Generally, wire 954 is thicker than loop 952 and is crimped thereto at 955 via a swaging procedure.

Wire 954 is slidable longitudinally through sheath member 950, while the sheath is longitudinally insertable through a biopsy channel of an endoscope insertion member (not shown). A flexible web member 956 is connected to loop 952 essentially around a circumference thereof to form a capture pocket, loop 952 defining a mouth opening of the pocket. More specifically, web member 956 is slidably attached to loop 952 along a proximal portion 958 thereof via a plurality of spaced thread ringlets 960. Web member 956 is fixedly but removably attached to loop 952 along a distal portion 962 thereof to enable at least a substantial separation of web member 956 from loop 952 upon a proximally directed cutting stroke of wire 954 during a cauterizing phase of an endoscopic polyp removal operation. As illustrated particularly in FIG. 25, web member 956 is fixed to distal end portion 962 at a plurality of discrete points 964 along a radially outer surface of loop 952. Those attachment points 964 are severable or rupturable, e.g., by the heat of cauterization, so that web member 956 is separated from loop 952 during cauterization.

As further illustrated in FIG. 25, a purse string 966 is attached to web member or pouch 956 along a ring shaped locus proximately to the mouth opening, that is, proximately to loop 952. Purse string 966 is attached at a proximal end to at least one of wire 954 and tubular member 950, as described hereinabove with reference to FIGS. 17A–17C, and 23–24. Purse string 966 is made of a heat-resistant material such as quartz and is attached to wire 954 proximally to the point of connection 955 of loop 952 to wire 954. Because quartz is prone to fracture, it is fixed to wire 954 via a reservoir of adhesive activated by ultraviolet radiation. It is to be noted that the length of purse string 966 must be selected so that the purse string does not close too early during a retraction of loop 952 into tubular sheath member 950. It is to be further noted that the embodiment of FIG. 25 is advantageously provided with the tether 930, 932, 942 of FIG. 23. The tether is omitted in FIG. 25 for purposes of clarity of illustration.

Figure 26:
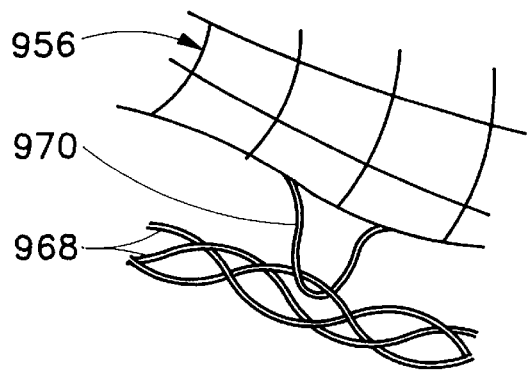
FIG. 26 is a partial schematic perspective view, on a large scale, showing a technique of fastening the capture pocket or pouch of FIG. 25 to the cauterization loop.
Figure 27:
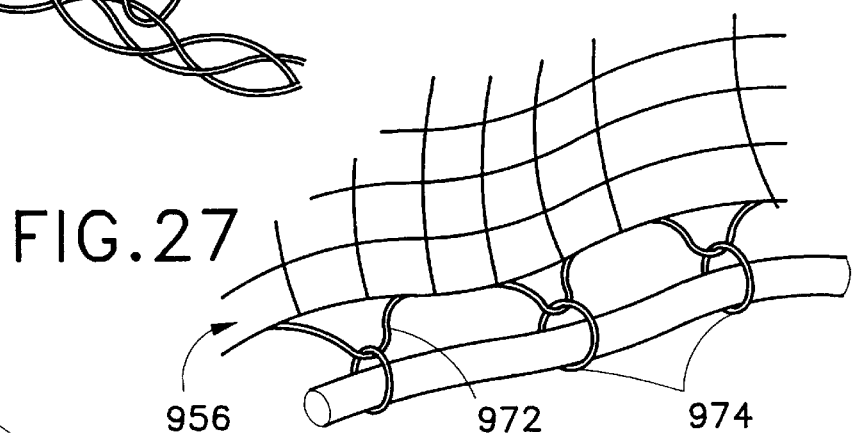
FIG. 27 is a partial schematic perspective view, on a large scale, depicting another technique of attaching the capture pocket or pouch of FIG. 25 to the cauterization loop.

As depicted in FIG. 26, where cauterization loop 952 comprises a plurality of metal strands or filaments 968 wound, woven or braided to one another, web member or capture pouch 956 may be attached to the loop via threads 970 inserted under individual strands or filaments 968 of loop 952. Alternatively, as shown in FIG. 27, web member or capture pouch 956 may be attached to loop 952 via threads 972 and minute metal ringlets 974. Ringlets 974 may become virtually integral with loop 952. In yet another attachment method, indicated in FIG. 28, web member or capture pouch 956 is attached to the radially outer surface of loop 952 along distal portion 962 thereof via an adhesive layer 976.

Generally, it is contemplated that distal portion 962 extends approximately one-third the length of loop 952, while proximal portion 958 extends approximately two-thirds the length of loop 952. Prior to the cutting and cauterizing phase of a polyp removal procedure, thread ringlets 960 slide back and forth along loop 952 as the loop is alternately extended and retracted into tubular sheath member 950 during attempts to properly position loop 952 relative to a polyp. During the cutting and cauterizing phase of the procedure, only distal portion 962 of loop 952 comes into contact with a polyp; the proximal portion 958 is retracted into tubular member 950 prior to the conduction of cauterization current.

The snare assembly of FIGS. 25–28 is designed to solve a problem arising with other snare designs where the web member or pouch is woven onto the cauterization loop. In use, when such a snare closes upon a polyp, the attachment ringlets or threads of the pouch slide towards the distal end of the snare and are interposed between the cauterization loop and the polyp. Thus, the cauterization loop has to cut through the attachment ringlets or threads of the pouch while cutting through the polyp. This may occasionally hinder a polypectomy operation.

Figure 28:
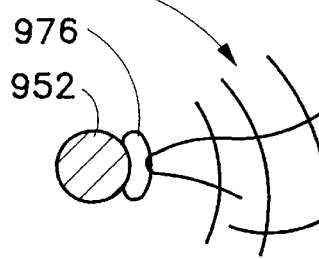
FIG. 28 is a partial schematic cross-sectional view, on a large scale, illustrating yet another technique of attaching the capture pocket or pouch of FIG. 25 to the cauterization loop.

In the design of FIGS. 25, 26 and 28, web member or pouch 956 is attached to loop 952 only along an outer surface thereof at distal portion 962. This attachment of web member or pouch 956 to the cauterization loop 952 cannot interfere with the cutting and cauterizing of a polyp. Where fine metal loops or filaments 974 are used to attach pouch 956 to cauterization loop 952 (FIG. 27), the metal filaments do not interfere with the cauterization process.

The sliding attachment of web member or pouch 956 to proximal portion 958 of cauterization loop 952 enables a repositioning of the snare relative to a polyp. More specifically, after loop 952 has been partially drawn back into tubular member 950, the loop can be shifted again in a distal direction relative to tubular member 950 to enable an adjustment in the position of the snare relative to the polyp. Web member or capture pouch 956 slides along the proximal portion 958 of loop 952 during these adjustments.

Accordingly, in the design of FIGS. 25, 26 and 28, a clean cut is obtained through a polyp, the snare may be repositioned relative to the polyp, and pouch 956 remains outside of tubular member 950 after severing of the polyp. Pouch 956 is severed from cauterization loop 952 during the polypectomy operation. The heat generated during the procedure severs ringlets 960 and releases pouch 956 occurs so that the pouch is held only by purse string 966.

Figure 29:
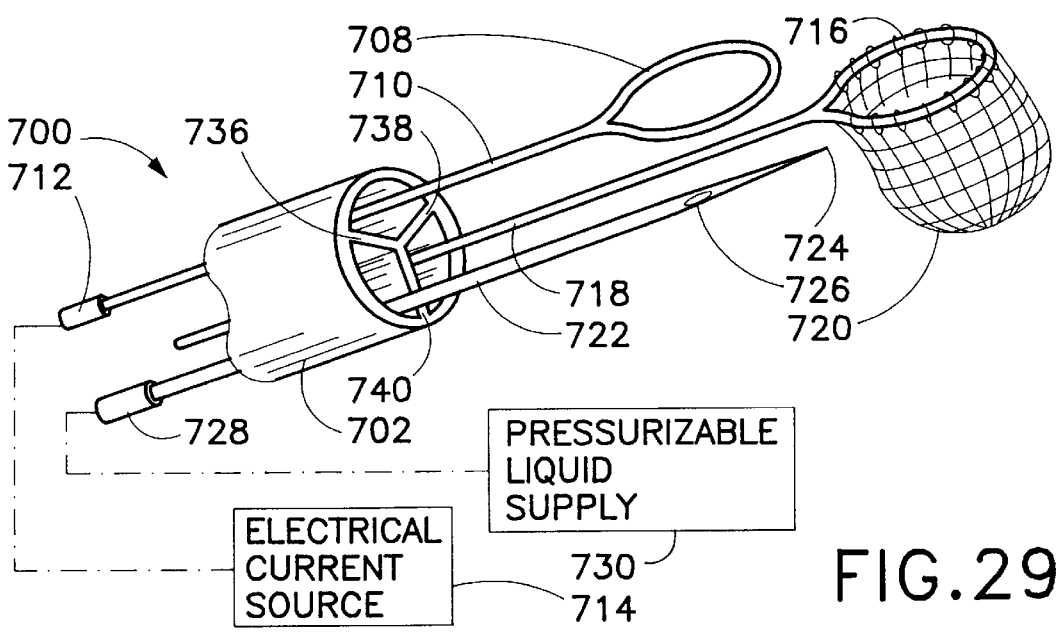
FIG. 29 is a schematic partial perspective view, on an enlarged scale, of an endoscopic instrument assembly for removing flat or nonprojecting polyps, in accordance with the present invention.

As illustrated in FIG. 29, an endoscopic instrument assembly 700 for use in severing and retrieving a flat or nonprojecting polyp from a wall of a colon or other internal organ comprises a tubular member 702 having a diameter sufficiently small so that the tubular member can be inserted through a biopsy channel 704 of a flexible endoscope 706 (FIGS. 30A–30D). Assembly 700 includes a cauterization loop 708 and an electrically conductive wire 710 operatively connected to the cauterization loop, the cauterization loop and the wire being disposed at least partially in tubular member 702. An electrical connector 712 is operatively connected to wire 710 for feeding an electrical current from a current source 714 to cauterization loop 708 via the wire. Assembly 700 further includes an auxiliary loop 716 provided at a distal end of an elongate flexible shifting member 718. Auxiliary loop 716 and shifting member 718 are at least partially disposed in tubular member 702. A flexible web member 720 is connected to auxiliary loop 716 so as to form a capture pocket, the auxiliary loop defining a mouth opening of the pocket. Assembly 700 also includes an elongate flexible tube 722 provided at a distal end with a needle point 724 and an aperture 726. Tube 722 is disposed at least partially in tubular member 702 and is provided at a proximal end with a fluid feed connector 728 for coupling the tube to a pressurizable liquid supply 730, whereby fluid is fed to tube 722 for ejection through aperture 726.

Figure 30A:
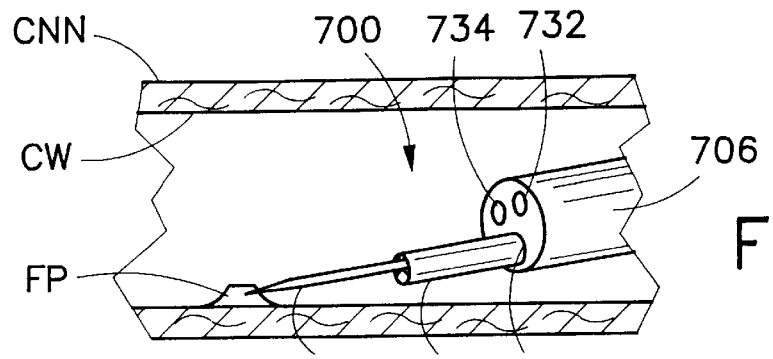
FIGS. 30A–30D are schematic partial perspective views of an endoscope with the instrument assembly of FIG. 29, showing successive steps in the use of the assembly to remove a flat or nonprojecting polyp, in accordance with the present invention.
Figure 30B:
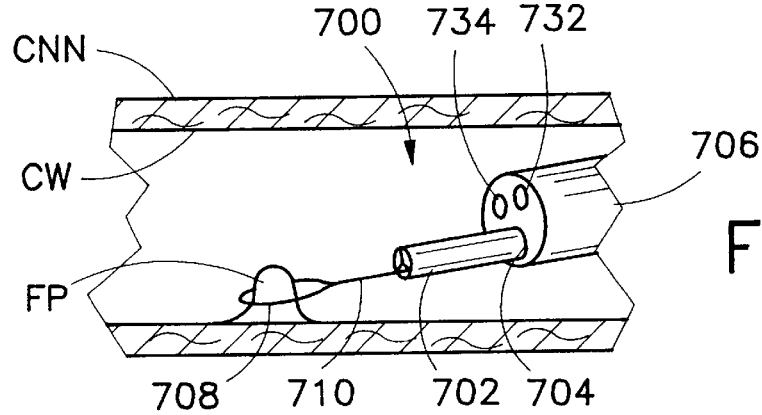
Figure 30C:
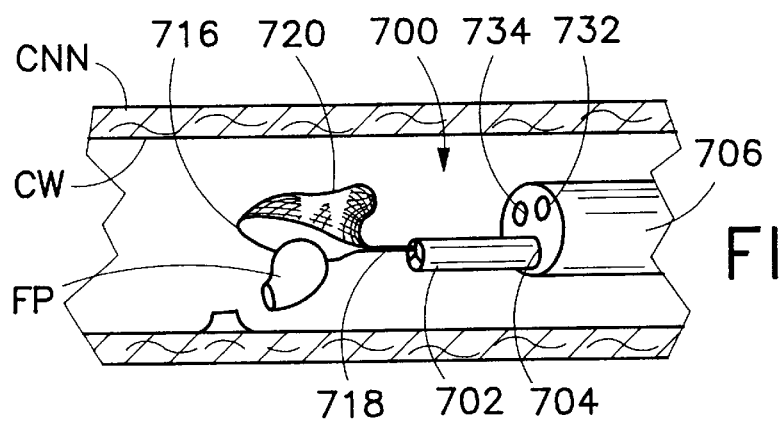
Figure 30D:
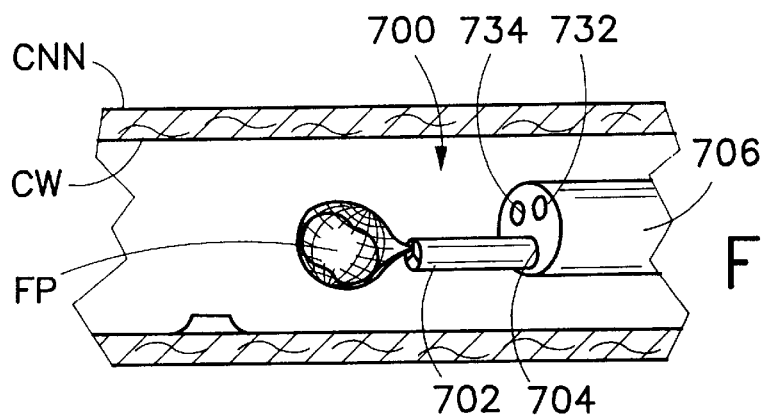

FIGS. 30A–30D depict successive steps in the use of instrument assembly 700 during an endoscopic tissue removal operation. Tubular member 702 is slidably disposed in biopsy channel 704 prior to or after the insertion of endoscope 706 into a colon CNN of a patient. Endoscope 706 and particularly an illumination guide 732 and fiber-optic image guide 734 thereof are used to visually monitor internal body tissues along the wall WC of colon CNN. Upon a detection of what appears to be a flat or nonprojecting polyp FP along colon wall WC, tubular member 702 is shifted in the distal direction to eject a distal end portion of the tubular member from biopsy channel 704. In addition, tube 722 is shifted in the distal direction to eject needle point 724 from tubular member 702. As shown in FIG. 30A, needle point 724 and aperture 726 are inserted into the polyp FP, for example, at the base thereof. Liquid is then transferred through tube 722 from supply 730 and forced out through aperture 726 into polyp FP to expand the polyp and thereby induce the polyp to stand away from colon wall WC, as shown in FIG. 30B.

After polyp FP is induced to stand away from wall WC, tube 722 is retracted back into tubular member 702 and cauterization loop 708 is ejected, expanded from a collapsed configuration and placed about the expanded polyp, as shown in FIG. 30B. Cauterization loop 708 is then closed, by moving tubular member 702 further in the distal direction to draw a portion of loop 708 back into the tubular member. Subsequently, an electrical current is conducted from source 714 along wire 710 to cauterization loop 708 to sever the expanded polyp FP.

After the severing of polyp FP, cauterization loop 708 is pulled in the proximal direction, relative to tubular member 702, to retract the cauterization loop back into tubular member 702. Then, shifting member 718 is pushed distally to eject auxiliary loop 716 and web member or pocket 720 from tubular member 702, as illustrated in FIG. 30B. Auxiliary loop 716 opens naturally in response to internal spring biasing forces, whereupon loop 716 and web or pocket member 720 is placed about severed polyp FP. Alternatively, it is possible to place the auxiliary loop 716 and web member 720 about polyp FP prior to the severing thereof by cauterization loop 708. In either case, after the severing of the expanded polyp FP by cauterization loop 708, auxiliary loop 716 is at least partially closed to capture the expanded and severed polyp in the pocket. Loop 716 is closed by pushing tubular member 702 in the distal direction about a proximal end portion of the auxiliary loop.

Figure 31:
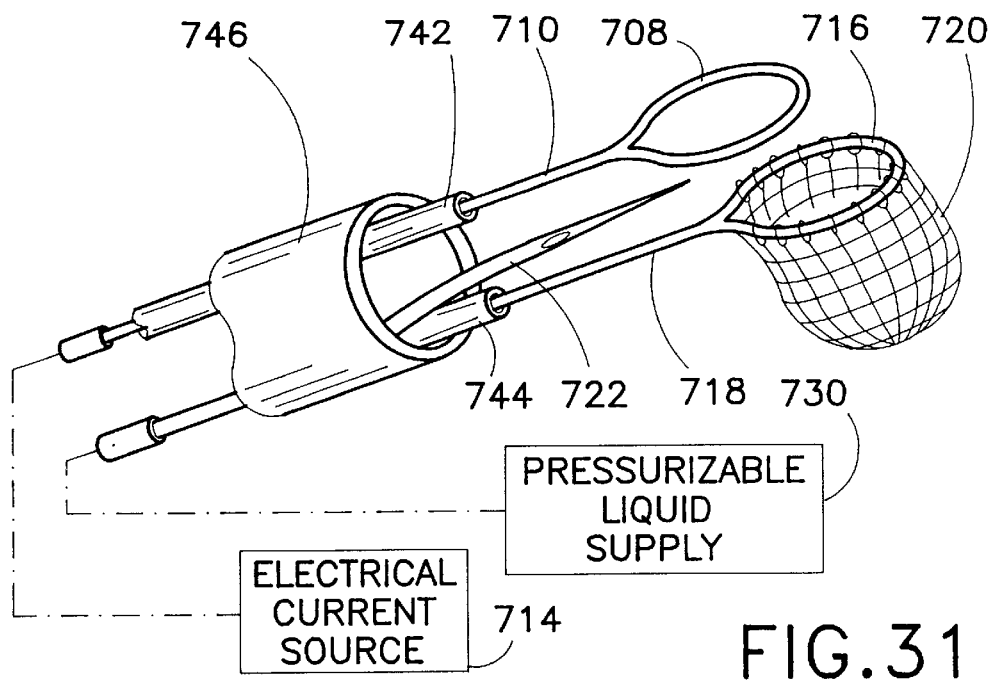
FIG. 31 is a schematic partial perspective view, on an enlarged scale, of another endoscopic instrument assembly for removing flat or nonprojecting polyps, in accordance with the present invention.

As depicted in FIG. 29, the different instruments of assembly 700 are disposed in respective lumens (not designated) of tubular member 702 defined by a plurality of septums 736, 738 and 740 joined to one another in a Y configuration. In an alternative construction, shown in FIG. 31, wire 710 and shifting member 718 are slidably disposed in respective ancillary tubes 742 and 744 in turn slidably disposed in an outer tubular member 746. Tubular member 746 need not be provided with septums 736, 738 and 740 (FIG. 29). Although tubes 722, 742 and 744 could be disposed directly in biopsy channel 704 (FIGS. 30A–30D) without tubular member 746, transportation, storage and use of the instrument assembly of FIG. 29 are facilitated if tubular member 746 is included.

Figure 32:
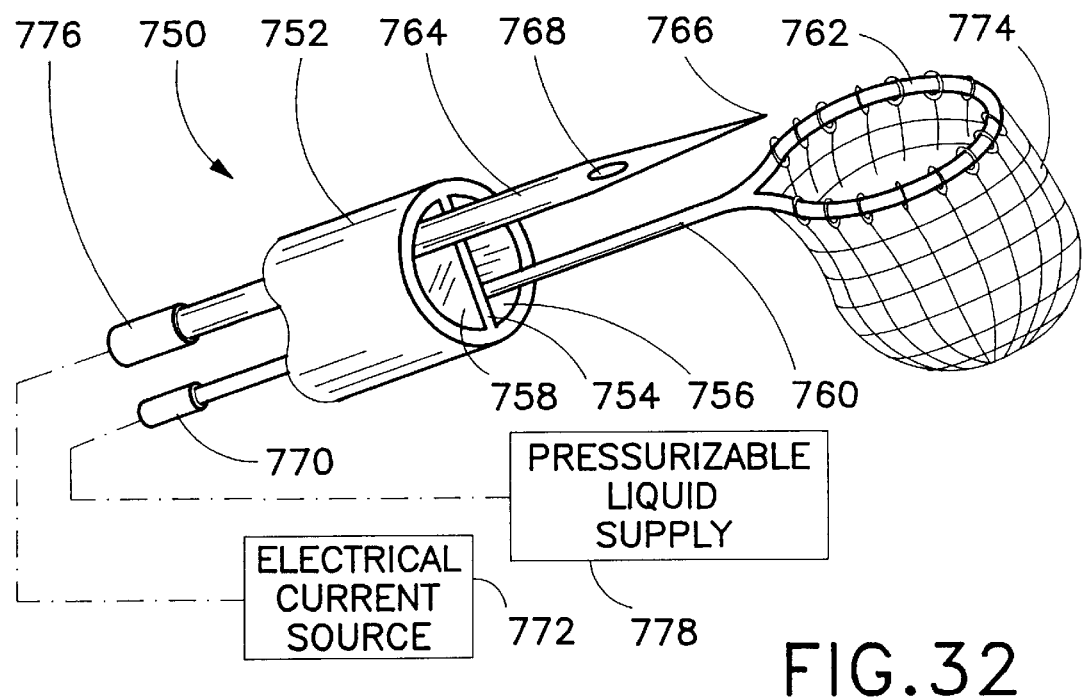
FIG. 32 is a schematic partial perspective view, on an enlarged scale, of yet another endoscopic instrument assembly for removing flat or nonprojecting polyps, in accordance with the present invention.

As illustrated in FIG. 32, another surgical instrument assembly 750 for use in snare cauterization operations comprises a tubular member 752 having a diameter sufficiently small so that the tubular member can be inserted through a biopsy channel of a flexible endoscope. Tubular member 752 is provided with a diametric and longitudinally extending septum 754 defining a pair of lumens 756 and 758. Lumen 756 is slidably traversed by an electrically conductive wire 760 operatively connected at a distal end to a cauterization loop 762, while lumen 758 is slidably traversed by a flexible fluid feed tube 764 provided at a distal end with a needle point 766 and a fluid outlet aperture 768. Wire 760 is provided at a proximal end with an electrical connector 770 operatively connected to an electrical current source 772. A flexible web member 774 is connected to cauterization loop 762 so as to form a capture pocket. A fluid feed connector 776 couples tube 764 to a pressurizable fluid supply 778 such as a syringe. Prior to an operation, cauterization loop 762 and needle point 766 are disposed within their respect lumens 756 and 758.

The use of instrument assembly 750 during an endoscopic polyp removal operation is a variation of that described above with reference to FIGS. 30A–30D, the variation resulting from the attachment of web member or capture pocket 774 to cauterization loop 762. Web member or capture pocket 774 is disposed about the expanded polyp FP simultaneously with the placement of cauterization loop 762 about the polyp. Pocket 774 is closed about polyp FP by the same distal motion of tubular member 752 that closes cauterization loop 762. The polyp is automatically captured upon severing of the polyp.

It is to be noted that web members or capture pockets 720 and 774 may be provided with one or more flexible tensile members 930 and 932 (FIGS. 23 and 24) as described above, for purposes of facilitating a repeated extension of auxiliary loop 716 or cauterization loop 762 from the respective tubular member and a concomitant opening and partial closing of web members or capture pockets 720 and 774, to enable optimal positioning of the loops about the polyp FP prior to a cauterization and severing procedure.

It is to be noted that the liquid used to expand a flat polyp, as described above with reference to FIG. 29 et seq. may have a color or hue so that the liquid also functions as a marker for purposes of correlating severed polyps with their respective locations on the wall of the colon prior to removal. Where two or more polyps are to be removed from the colon, the polyps (and their necks or stalks) are marked with respective colors to differentiate them from each other. The tube which is used to inject the dyes is flushed out with transparent saline between successive marking (and possible polyp expanding) operations.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A surgical instrument assembly for use in snare cauterization operations, comprising:
   a tubular member;
   a cauterization loop;
   an electrically conductive wire operatively connected to said cauterization loop, said cauterization loop and said wire being disposed at least partially in said tubular member;
   an auxiliary loop;
   an elongate flexible shifting member connected at one end to said auxiliary loop, said auxiliary loop and said shifting member being at least partially disposed in said tubular member;
   a flexible web member connected to said auxiliary loop so as to form a capture pocket, said auxiliary loop defining a mouth opening of said pocket; and
   an elongate flexible tube provided at a distal end with a needle point and an aperture, said flexible tube being disposed at least partially in said tubular member.

2. The instrument assembly defined in claim 1, further comprising a first additional flexible tube and a second additional flexible tube each extending slidably through said tubular member, said cauterization loop and said wire being disposed at least partially in said first additional flexible tube, said auxiliary loop and said shifting member being at least partially disposed in said second additional flexible tube.

3. The instrument assembly defined in claim 2 wherein said tubular member is provided with at least two septums defining at least three separate longitudinally extending lumens, the flexible tubes extending through respective ones of said lumens.

4. The instrument assembly defined in claim 1 wherein said tubular member is provided with at least two septums defining at least three separate longitudinally extending lumens, said cauterization loop and said wire being disposed at least partially in a first one of said lumens, said auxiliary loop and said shifting member being at least partially disposed in a second one of said lumens, said flexible tube being disposed at least partially in a third one of said lumens.

5. The instrument assembly defined in claim 1, further comprising at least one flexible tensile member connected to said flexible web member at a proximal end thereof and to said tubular member at a point spaced from a distal end thereof.

6. The instrument assembly defined in claim 1 wherein said web member is slidably connected to said auxiliary loop at a plurality of spaced locations.

7. The instrument assembly defined in claim 1 wherein said flexible web member is a net.

8. The instrument assembly defined in claim 1 wherein said flexible web member is a continuous film of polymeric material.

9. The instrument assembly defined in claim 1 wherein said web member is disposed in a collapsed configuration together with said auxiliary loop inside said tubular member.

10. A surgical instrument assembly for use in snare cauterization operations, comprising:
   a tubular member;
   a cauterization loop;
   an electrically conductive wire operatively connected to said cauterization loop, said cauterization loop and said wire being disposed at least partially in said tubular member;
   a flexible web member connected to said cauterization loop so as to form a capture pocket, said cauterization loop defining a mouth opening of said pocket; and
   an elongate flexible tube provided at a distal end with a needle point and an aperture, said flexible tube being disposed at least partially in said tubular member.

11. The instrument assembly defined in claim 10, further comprising an additional flexible tube extending slidably through said tubular member, said cauterization loop and said wire being disposed at least partially in said additional flexible tube.

12. The instrument assembly defined in claim 11 wherein said tubular member is provided with at least one septum defining at least two separate longitudinally extending lumens, the flexible tubes extending through respective ones of said lumens.

13. The instrument assembly defined in claim 10 wherein said tubular member is provided with at least one septum defining at least two separate longitudinally extending lumens, said cauterization loop and said wire being disposed at least partially in a first one of said lumens, said flexible tube being disposed at least partially in a second one of said lumens.

14. A method for removing a selected portion of internal body tissues of a patient, comprising the steps of:
   providing (i) a flexible conductive cauterization loop, (ii) a flexible tube provided at a distal end with a needle point and an aperture, and (iii) a flexible auxiliary loop to which a flexible web member is connected to define an expandable pocket, said cauterization loop, said flexible tube and said auxiliary loop being disposed in a common tubular member;
   inserting said tubular member into a patient;
   after insertion of said tubular member into the patient, shifting said flexible tube in a distal direction to eject said needle point from said tubular member;
   inserting said needle point and said aperture into the selected internal tissues of the patient, the selected internal tissues being disposed along an internal organic wall of the patient;
   forcing liquid through said flexible tube and said aperture into the selected internal tissues of the patient to expand the tissues and thereby induce the tissues to stand away from said internal organic wall;
   shifting said cauterization loop in a distal direction relative to said tubular member to eject said cauterization loop from said tubular member;
   upon ejection of said cauterization loop from said tubular member, at least partially expanding said cauterization loop from a collapsed configuration;
   manipulating the expanded cauterization loop from outside of the patient to pass the expanded cauterization loop over the expanded internal tissues of the patient;
   upon a passing of the expanded cauterization loop over the expanded internal tissues, closing the cauterization loop about the expanded internal tissues;
   conducting an electrical current along said wire and to the closed cauterization loop to sever the expanded internal tissues;
   ejecting said auxiliary loop from said tubular member;
   upon ejection of said auxiliary loop from said tubular member, at least partially opening said auxiliary loop from a folded configuration;
   maneuvering the opened auxiliary loop from outside of the patient to pass the opened auxiliary loop over the expanded internal tissues so that said web member substantially surrounds the expanded internal tissues; and
   upon the severing of the expanded internal tissues by said cauterization loop and upon maneuvering of the auxiliary loop over the expanded internal tissues, at least partially closing said auxiliary loop to capture the severed internal body tissues in said pocket.

15. The method defined in claim 14 wherein the closing of said cauterization loop about the expanded internal tissues is effectuated by a relative motion of said tubular member and said cauterization loop towards one another and a resultant partial drawing of said cauterization loop into said tubular member.

16. The method defined in claim 14 wherein the closing of said auxiliary loop about the expanded internal tissues is effectuated by a relative motion of said tubular member and said auxiliary loop towards one another and a resultant partial drawing of said auxiliary loop into said tubular member.

17. A method for removing a selected portion of internal body tissues of a patient, comprising the steps of:
   providing (i) a flexible conductive cauterization loop to which a flexible web member is connected to define an expandable pocket, and (ii) a flexible tube provided at a distal end with a needle point and an aperture, said cauterization loop, said flexible tube and said web member being disposed in a common tubular member;
   inserting said tubular member into a patient;
   after insertion of said tubular member into the patient, shifting said flexible tube in a distal direction to eject said needle point from said tubular member;
   inserting said needle point and said aperture into the selected internal tissues of the patient, the selected internal tissues being disposed along an internal organic wall of the patient;
   forcing liquid through said flexible tube and said aperture into the selected internal tissues of the patient to expand the tissues and thereby induce the tissues to stand away from said internal organic wall;

shifting said cauterization loop in a distal direction relative to said tubular member to eject said cauterization loop from said tubular member;

upon ejection of said cauterization loop from said tubular member, at least partially expanding said cauterization loop and said web member from a collapsed configuration;

manipulating the expanded cauterization loop from outside of the patient to pass the expanded cauterization loop and the expanded web member over the expanded internal tissues of the patient;

upon a passing of the expanded cauterization loop and the expanded web member over the expanded internal tissues, closing the cauterization loop about the expanded internal tissues; and conducting an electrical current along said wire and to the closed cauterization loop to sever the expanded internal tissues.

18. The method defined in claim 17 wherein the closing of said cauterization loop about the expanded internal tissues is effectuated by a relative motion of said tubular member and said cauterization loop towards one another and a resultant partial drawing of said cauterization loop into said tubular member.

* * * * *